US006800740B1

(12) United States Patent
Cunningham et al.

(10) Patent No.: US 6,800,740 B1
(45) Date of Patent: Oct. 5, 2004

(54) VARIANTS OF NATIVE GROWTH HORMONES HAVING NON NATURALLY OCCURRING AMINO ACID SEQUENCES OR COVALENT MODIFICATIONS

(75) Inventors: Brian C. Cunningham, Piedmont, CA (US); James A. Wells, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 1148 days.

(21) Appl. No.: 08/479,883

(22) Filed: Jun. 7, 1995

Related U.S. Application Data

(60) Division of application No. 08/122,548, filed as application No. PCT/US92/03743 on May 6, 1992, now Pat. No. 5,506,107, which is a continuation-in-part of application No. 07/864,120, filed on Apr. 6, 1992, now abandoned, which is a continuation-in-part of application No. 07/698,753, filed on May 10, 1991, now abandoned.

(51) Int. Cl.$^7$ .................. A61K 38/27; C07K 14/61; C07K 14/475

(52) U.S. Cl. .................. 530/399; 530/402; 514/12

(58) Field of Search .................. 530/399, 402; 514/12

(56) References Cited

U.S. PATENT DOCUMENTS

| | | | |
|---|---|---|---|
| 4,782,139 A | * 11/1988 | DiMarchi et al. ........... | 530/407 |
| 4,857,637 A | 8/1989 | Hammonds et al. | |
| 4,871,835 A | * 10/1989 | Aviv et al. .................. | 530/399 |
| 5,073,540 A | 12/1991 | Olsson ......................... | 514/3 |
| 5,350,836 A | 9/1994 | Kopchick et al. ........... | 530/399 |
| 5,534,617 A | * 7/1996 | Cunningham ............... | 530/399 |
| 5,580,723 A | * 12/1996 | Wells et al. .................. | 435/6 |
| 5,681,809 A | * 10/1997 | Kopchick et al. ........... | 514/2 |
| 6,238,915 B1 | 5/2001 | Chihara | |

FOREIGN PATENT DOCUMENTS

| | | |
|---|---|---|
| EP | 0 103 395 | 3/1984 |
| EP | 0 333 348 | 9/1989 |
| EP | 0 333 349 | 9/1989 |
| GB | 2 073 245 | 10/1981 |
| WO | WO 86/01229 | 2/1986 |
| WO | WO 88/07084 | 9/1988 |
| WO | WO 90/04788 | 5/1990 |
| WO | WO 90/05185 | 5/1990 |
| WO | WO 91/02754 | 3/1991 |
| WO | WO 91/05853 | 5/1991 |
| WO | WO 92/09690 | 6/1992 |
| WO | WO 92/19736 | 11/1992 |
| WO | WO 93/00109 | 1/1993 |
| WO | WO 96/21029 | 11/1995 |

OTHER PUBLICATIONS

Elberg et al., "Mitogenic and Binding Properties of Monoclonal Antibodies to the Prolactin Receptor in Nb$_2$ Rat Lymphoma Cells," *Journal of Biological Chemistry*, 265:25:14770–14776 (1990).

Okamura et al., "Characterization and Applications of Monoclonal Antibodies to the Prolatin Receptor," *Endocrinology*, 124:5:2499–2508 (1989).

Sissom et al., "Anti–Growth Action on Mouse Mammary and Prostate Glands of a Monoclonal Antibody to Prolactin Receptor," *American Journal of Pathology*, 133:3:589–595 (1988).

Nicoll, C., et al., "Structural Features of Prolactins and Growth Hormones That Can Be Related to Their Biological Properties", *Endocrine Reviews*, 7:169–203 (1986).

Barnard, "Monoclonal Antibodies to the Rabbit Liver Growth Hormone Receptor: Production and Characterization", *Endocrinology* 115:5:1805–1813 (1984).

Barnard, "Evidence from the use of monoclonal antibody probes for structural heterogeneity of the growth hormone receptor", *Biochem J.* 231:459–468 (1985).

Seaver, "Monoclonal Antibodies in Industry: More Difficult Than Originally Thought", *Gen. Eng. News* 14:10 & 21 (Aug., 1994).

Waters et al., "Studies with Anti–Growth Hormone Receptor Antibodies", *Journal of Biological Chemistry* 254:14:6826–6832 (1979).

Cunningham, B., et al., "Rational design of receptor–specific variants of human growth hormone", *Proc. Natl. Acad. Sci.* 88:3407–3411 (1991).

Ashkenazi, A., et al., "Comparative Study of in Vitro and in vivo Modulation of Lactogenic and Somatotrophic Receptors by Native Human Growth Hormone and Its Modified Analog Prepared by Recombinant Deoxyribonucleic Acid Technology," *Endocrinology* 121:414–419 (1987).

Aston, R., et al., "Antigenic Structure of Bovine Growth Hormone: Location of a Growth Enhancing Region," *Molecular Immunology*, 28:41–50 (1991).

Bamborough, P., et al., "Predictive Modelling of the 3–D Structure of Interleukin–13," *Protein Engineering* 7:1077–1082 (1994).

Bamborough, P., et al., "A Computer Model of the Interleukin–4/Receptor Complex," *Proteins, Structure, Function & Genetics* 17:11–19 (1993).

(List continued on next page.)

Primary Examiner—Christine J. Saoud
(74) Attorney, Agent, or Firm—Gates & Coooper LLP

(57) ABSTRACT

Growth hormones contain two receptor binding sites termed site 1 and site 2 with which they form ternary complexes with their receptors. In this scheme, site 1 on the hormone binds to one molecule of receptor and then site 2 binds to another molecule of receptor, thereby producing a 1:2 complex. Disclosed herein are growth hormone variants consisting of modifications to the native sequence in the region of site 1 or site 2, or alternatively a combination of modifications at both site 1 and site 2.

25 Claims, 18 Drawing Sheets

OTHER PUBLICATIONS

Bass, S., et al., "A systematic mutational analysis of hormone–binding determinants in the human growth hormone receptor," *Proc. Natl. Acad. Sci.* 88:4498–4502 (1991).

Binder, L., et al., "Site–Directed Mutations of Human Growth Hormone that Selectively Modify Its Lactogenic Activity and Binding Properties," *Molecular Endocrinology* 4:1060–1068 (1990).

Chen, W., et al., "Functional Antagonism between Endogenous Mouse Growth Hormone (GH) and a GH Analog Results in Dwarf Transgenic Mice," *Endocrinology* 129:1402–1408 (1991).

Chen, W., et al., "Glycine 119 of Bovine Growth Hormone is Critical for Growth–Promoting Activity," *Molecular Endocrinology* 5:1845–1852 (1991).

Chen, W., et al., "Mutations in the Third α–Helix of Bovine Growth Hormone Dramatically Affect Its Intracellular Distribution in Vitro and Growth Enhancement in Transgenic Mice," *J. Biol. Chem.* 266:2252–2258 (1991).

Chen, W., et al., "Expression of a mutated bovine growth hormone gene suppresses growth of transgenic mice," *Proc. Natl. Acad. Sci.* 87:5061–5065 (1990).

Chiba, S., et al., "Identification and Cellular Distribution of Distinct Proteins Forming Human GM–CSF Receptor," *Cell Regulation* 1:327–335 (1990).

Cosman, D., et al., "A new cytokine receptor superfamily," *TIBS* 15:265–270 (1990).

Cunningham, B., et al., "High–Resolution Epitope Mapping of hGH–Receptor Interactions by Alanine–Scanning Mutagenesis," *Science* 244:1081–1085 (1989).

Cunningham, B., et al., "Engineering Human Prolactin to Bind to the Human Growth Hormone Receptor," *Science* 247:1461–1465 (1990).

Cunningham, B., et al., "Dimerization of the Extracellular Domain of the Human Growth Hormone Receptor by a Single Hormone Molecule," *Science* 254:821–8215 (1991).

Davis, S., et al., "LIFRβ and gp 130 as Heterodi– merizing Signal Transducers of the Tripartite CNTF Receptor," *Science* 260:1805–1808 (1993).

Demchuk, E., et al., "Receptor Binding Properties of Four–Helix–Bundle Growth Factors Deduced From Electrostatic Analysis," *Protein Science* 3:920–935 (1994).

Devos, R., et al., "Molecular Basis of a High Affinity Murine Interleukin–5 Receptor," *The EMBO Journal* 10:2133–2137 (1991).

de Vos, A., et al., "Human Growth Hormone and Extracellular Domain of Its Receptor: Crystal Structure of the Complex", *Science* 255:306–312 (1992).

Diederichs, K., et al., "Novel Fold and Putative Receptor Binding Site of Granulocyte–Macrophage Colony–Stimulating Factor," *Science* 254:1779–1782 (1991).

Fuh, G., et al., "Mechanism–Based Design of Prolactin Receptor Antagonists," *J. Biol. Chem.* 268:5376–5381 (1993).

Fuh, G., et al., "Rational Design of Potent Antagonists to the Human Growth Hormone Receptor," *Science* 256:1677–1680 (1992).

Gooley, P., et al., Location of an α–Helix in Fragment 96–133 from Bovine Somatotropin by $^1$H NMR Spectroscropy, *Biochemistry* 27:4032–4040 (1988).

Gunther, N., et al., "The Secreted Form of the Epidermal Growth Factory Receptor," *J. Biol. Chem.* 265:22082–22085 (1990).

Haniu, M., et al., "Recombinant Human Erythropoietin (rHuEPO): Cross–linking With Disuccinimidyl Esters and Identification of the Interfacing Domains in EPO," *Protein Science* 2:1441–1452 (1993).

Heldin, C., et al., "Dimerization of B–type Platelet–derived Growth Factor Receptors Occurs after Ligand Binding and Is Closely Associated with Receptor Kinase Activation," *J. Biol. Chem.* 264:8905–8912 (1989).

Kadar, T., et al., "Decrease in Prolactin Receptor Affinity in the Rat Mammary Tumor Model After Treatment with Analogs of Samatostatin and LH–RH," *Chemical Abstracts* 110 (1989).

Kondo, M., et al., "Sharing of the Interleukin–2 (IL–2) Receptor γ Chain Between Receptors for IL–2 and Il–4," *Science* 262:1874–1877 (1993).

Kostyo, J., "The Multivalent Nature of Growth Hormone," *Human Growth Hormone* 33:449–453 (1986).

Lambert, G., et al., "Crystallization and Preliminary X–ray Diffraction Studies of a Complex between Interleukin–2 and a Soluble Form of the p55 Component of the High Affinity Interleukin–2 Receptor," *J. Biol. Chem.* 264:12730–12736; (1989).

Leroy–Martin, B., et al., "Modulation of Prolactin Receptors (PRL–R) by Lactogenic and Steroid Hormones in Human Breast Cancer Cells in Long–Term Tissue Culture," *Chemical Abstracts* 111:110 (1989).

Lokker, N., et al., "Structure–Activity Relationship Study of Human Interleukin–3," *J. Biol. Chem.* 266:10624–10631 (1991).

Lowman, H., et al., "Mutational Analysis and Protein Engineering of Receptor–binding Determinants in Human Placental Lactogen," *J. Biol. Chem.* 266:10982–10988 (1991).

Miyajima, A., et al., "Common Subunits of Cytokine Receptors and the Functional Redundancy of Cytokines," *TIBS* 17 (1992).

Murakami, M., et al., "IL–6–Induced Homodimerization of gph 130 and Associated Activation of a Tyrosine Kinase," *Science* 260:1808–1810 (1993).

Nicola N., et al., "Subunit Promiscuity Among Hemopoietic Growth Factor Receptors," *Cell* 67:1–4 (1991).

Noguchi, M., et al., "Interleukin–1 Receptor γ Chain: A Functional Component of the Interleukin–7 Receptor," *Science* 262:1877–1880 (1993).

Nowak, R., et al., "Bubble Boy Paradox Resolved," *Science* 262:1818 (1993).

Ogura, T., et al., "Molecular Mechanism for the Formation of the High–affinity Complex of Interleukin 2 and its Receptor," *Mol. Biol. Med.* 5:123–138 (1988).

Russell, S., et al., "Interleukin–2 Receptor γChain: A Functional Component of the Interleukin–4 Receptor," *Science* 262:1880–1883.

Russell, J., et al., "Recombinant Hormones from Fragments of Human Growth Hormone and Human Placental Lactogen," *J. Biol. Chem.* 256:296–300 (1981).

Salem, M., "Effects of the Amino–Terminal Portion of Human Growth Hormone on Glucose Clearance and Metabolism in Normal, Diabetic, Hypophysectomized, and Diabetic–Hypophysectomized Rats," *Endocrinology* 123:1565–1576 (1988).

Saragovi, H., et al., "The Murine Interleukin 2 Receptor," *J. Immunology* 139:1918–1926 (1987).

Savino, R., et al., "Generation of Interleukin–6 Receptor antagonists by Molecular–modeling Guided Mutagenesis of Residues Important for gph 130 Activation," *The EMBO Journal* 13:1357–1367 (1994).

Stahl, N., et al., "The Alphas, Betas, and Kinases of Cytokine Receptor Complexes," *Cell* 74:587–590 (1993).

Taga, T., et al., "Cytokine Receptors and Signal Transduction," *The FASEB Journal* 6:3387–3396 (1992).

Taga, T., et al., "Interleukin–6 Triggers the Association of its Receptor With a Possible Signal Transducer, gp130," *Cell* 58:573–581, (1989).

Teshigawara, K., et al., "Interleukin 2 High–Affinity Receptor Expression Requires Two Distinct Binding Proteins," *J. Exp. Med*. 165:223–238 (1987).

Ullrich, A., et al., "Signal Transduction by Receptors with Tyrosine Kinase Activity," *Cell* 61:203–212 (1990).

Watowich, S., et al., "Homodimerization and Constitutive Activation of the Erythropoietin Receptor," *Proc. Natl. Acad. Sci.* 89:2140–2144 (1992).

Wells, J., "Structural and Functional Basis for Hormone Binding and Receptor Oligomerization," *Current Opinion in Cell Biology* 6:163–174 (1994).

Wlodawer, A., et al., "Hematopoietic Cytokines: Similarities and Differences in the Structures, with Implications for Receptor Binding," *Protein Science* 2:1373–1382 (1993).

Zeppezauer, M., "Formation of Large Crystals," *Methods in Enzymology* 22:253–266 (1971).

\* cited by examiner

VARIANTS OF NATIVE GROWTH HORMONES HAVING NON NATURALLY OCCURRING AMINO ACID SEQUENCES OR COVALENT MODIFICATIONS

This is a divisional of U.S. patent application Ser. No. 08/122,548, filed Sep. 29, 1993, now U.S. Pat. No. 5,506,107, which is the U.S. national phase application of PCT/US92/03743, filed May 6, 1992, which is a continuation in part of U.S. application Ser. No. 07/864,120, filed Apr. 6, 1992, now abandoned, which is a continuation in part of U.S. patent application Ser. No. 07/698,753, filed May 10, 1991, now abandoned.

BACKGROUND OF THE INVENTION

1. Field of the Invention

This invention relates to the field of polypeptide ligand and receptor interactions. In particular, it relates to the field of selecting and screening antagonists and agonists for polypeptide ligands.

2. Description of the Background Art

Ligand induced receptor oligomerization has been proposed as a mechanism of signal transduction for the large family of tyrosine kinase receptors that contain an extracellular ligand binding domain (for reviews see Yarden, Y., et al., *Ann. Rev. Biochem* 57:443–478 (1988); Ullrich, A., et al., *Cell* 61:203–212 [1990]). In these models binding of one hormone molecule (or subunit) (H) per receptor (R) is thought to induce formation of an $H_2R_2$ complex. For example, crosslinking and non-dissociating electrophoretic studies suggest that epidermal growth factor (EGF) promotes dimerization of the EGF receptor followed by receptor autophosphorylation and activation of the intracellular tyrosine kinase (Shector, Y., et al., *Nature* 278:835–838 (1979); Schreiber, A. B., et al., *J. Biol. Chem.*, 258: 846–853 (1983); Yarden, Y., et al., *Biochemistry*, 26:1434–1442 (1987); Yarden, Y., et al., *Biochemistry* 26:1443–1451 (1987). Studies of other tyrosine kinase receptors including the insulin receptor (Kahn, C. R., et al., *Proc. Natl. Acad. Sci. USA* 75:4209–4213 (1978); Kubar J., et al., *Biochemistry* 28:1086–1093 (1989); Heffetz, D., et al., *J. Biol. Chem.* 261:889–894 (1986), platelet derived growth factor (PDGF) receptor (Heldin, C. H., et al., *J. Biol. Chem.* 264:8905–8912 (1989); Hammacher, A., et al., *EMBO J.* 8:2489–2495 (1989); Seifert, R. A., et al., *J. Biol., Chem.* 264:8771–8778 (1989)) and insulin-like growth factor (IGF-I) receptor (Ikari, N., et al., *Mol. Endocrinol.* 2:831–837.), indicate that oligomerization of the receptor is tightly coupled to the biological effect. Other groups have recently crystallized a polypeptide hormone in complex with its extracellular binding domain (Lambert, G., et al., *J. Biol. Chem.* 264:12730–12736 (1989); Gunther, N., et al., *J. Biol. Chem.* 265:22082–22085 (1990)). However, more detailed analyses of the structural perturbations and requirements for ligand induced changes in these or other receptors have been hampered because of the complexities of these membrane associated systems and the lack of suitable quantities of highly purified natural or recombinant receptors.

When purified receptors were available the assay procedures were often structured so that the nature of the hormone-receptor complex was not recognized. In U.S. Pat. No. 5,057,417, hGH binding assays were conducted using $^{125}$I-hGH competition with cold hGH for binding to the extracellular domain of recombinant hGH receptor (hGHbp), or hGH binding protein; the resulting complex was treated with antibody to the hGHbp, plus polyethylene glycol, to precipitate the complex formed. These immuno-precipitation assays suggested that hGH formed a 1:1 complex with hGHbp. This immunoprecipitation assay correctly detected the amount of $^{125}$I-hGH bound, but it incorrectly indicated a 1:1 molar ratio.

Various solid phase assays for hGH receptor and binding protein have been used. Such assays detected the amount of hGH bound but not the molar ratio of hGH to receptor. Binding assays with solid phase or with membrane fractions containing hGH receptor were not suitable for determining the molar ratio of hGH to receptor due to an inability to detect the total amount of active receptor and/or the amount of endogenous hGH bound. Based upon earlier work, such as with EGF, the art assumed the hGH-receptor complex would be an $H_2R_2$ tetramer.

The hGH receptor cloned from human liver (Leung, D. W. et al., *Nature*, 330:537 (1987)) has a single extracellular domain (~28 kD), a transmembrane segment, and an intracellular domain (~30 kD) that is not homologous to any known tyrosine kinase or other protein. Nonetheless, the extracellular portion of the hGH receptor is structurally related to the extracellular domains of the prolactin receptor (Boutin, J. M. et al., *Cell* 69:(1988)) and broadly to at least eight other cytokine and related receptors. hGHbp expressed in *Escherichia coli* has been secreted in tens of milligrams per liter (Fuh, G., et al., *J. Biol. Chem.*, 265:3111–3115 (1990)). The highly purified hGHbp retains the same specificity and high affinity for hGH ($K_D$ –0.4 nM) as compared to the natural hGHbp found in serum.

hGH is a member of an homologous hormone family that includes placental lactogens, prolactins, and other genetic and species variants of growth hormone (Nicoll, C. S., et al. *Endocrine Reviews*,7:169(1986). hGH is unusual among these in that it exhibits broad species specificity and binds to either the cloned somatogenic (Leung, D. W. et al. [1987] *Nature* 330: 537) or prolactin receptor (Boutin, J. M., et al. *Cell*, 53:69). The cloned gene for hGH has been expressed in a secreted form in *Eschericha coli* (Chang, C. N., et al., *Gene* 55:189 [1987]) and its DNA and amino acid sequence has been reported (Goeddel, et al. *Nature*,281:544 [1979); Gray, et al., *Gene* 39: 247[1985]). The three-dimensional structure of hGH has not previously been available. However, the three-dimensional folding pattern for porcine growth hormone (pGH) has been reported at moderate resolution and refinement (Abdel-Meguid, S. S. et al. *Proc. Natl. Acad. Sci. USA*, 84:6434 [1987]). hGH receptor and antibody binding sites have been identified by homolog-scanning mutagenesis (Cunningham, et al, *Science* 243:1330, 1989). GH with N-terminal amino acids deleted or varied are known. See Gertler, et al., *Endocrinology* 118:720 (1986), Ashkenazi, et al., *Endocrinology* 121:414 (1987), Binder, *Mol. Endo.*,7:1060–1068 (1990), and WO 90/05185. Antagonist variants of hGH are described by Chen, et al., *Mol. Endo.*, 5(10):1845 (1991) and literature set forth in the bibliography thereof; and WO 91/05853. hGH variants are disclosed by Cunningham, et al., *Science*, 244:1081 (1989) and *Science* 243:1330–1336 (1989).

Since the mode of interaction of many polypeptide ligands with their receptors has remained uncertain it has been difficult to engineer amino acid sequence variants of such ligands to achieve desired properties. Essentially, the art has introduced variation at random, perhaps in some cases with guidance from homology analyses to similarly-acting ligands or animal analogues, or from analysis of fragments, e.g., trypsin digest fragments. Then the art has screened the candidates for the desired activity, e.g., agonist or antagonist activity. The screening methods have been tedious and expensive, e.g., the use of transgenic animals (WO 91/05853). Methods are needed for improving the efficiency of selection of candidates. In particular, methods are needed for focusing on candidates likely to be either antagonists or agonists. Antagonists are substances that suppress, inhibit or interfere with the biological activity of a native ligand, while agonists exhibit greater activity per se than the native ligand.

It therefore is an object of this invention to provide improved methods for the efficient selection of agonist or antagonist polypeptide ligands.

It is another object herein to provide a method for detecting ligands that form sequential 1:2 complexes with their receptors.

Another object herein is to assay candidate substances for their ability to interfere with or promote the formation of such 1:2 ligand-receptor complexes.

An additional object is to provide amino acid sequence variants of polypeptide ligands that are capable of acting as agonists or antagonists.

Other objects, features and characteristics of the present invention will become more apparent upon consideration of the following description and the appended claims.

SUMMARY OF THE INVENTION

We have unexpectedly found that growth hormones and the class of conformational ligands to which they belong are capable of forming 1:2 complexes with their receptor in which a first ligand site, site 1, binds to one receptor and then a second ligand site, site 2, binds to another molecule of receptor, thereby yielding a 1:2 complex. The ligands to which this invention are applicable are monomeric ligands containing 4 amphipathic antiparallel alpha-helical domains separated and terminated at both ends by non-helical amino acid sequences. It is now possible by analogy to our work with growth hormone, prolactin and placental lactogen to efficiently design agonist or antagonist amino acid sequence variants of such ligands by introducing amino acid sequence variation into sites 1 and/or 2 as will be more fully described below.

The two-site complex formation assay is used to screen for substances which are ligand agonists or antagonists. Such substances are essentially unlimited and include organic, non-proteinaceous compounds as well as amino acid sequence variants of the ligands and binding protein or receptor variants.

New amino acid sequence variants of such alpha helical ligands also are described. In particular, antagonists for polypeptide ligands are provided which comprise an amino acid sequence mutation in site 2 which reduces or eliminates the affinity of the ligand for receptor at site 2. Ideally, the ligand antagonist analogue will have low or no affinity for receptor at site 2 and and will have elevated affinity for receptor at site 1.

Also provided herein are agonist ligand amino acid sequence variants having mutations at sites 1 and/or 2 which increase the ligand affinity for one or both sites. In prefered embodiments, the rate constants for both sites are selected such that the average residence time of the ligand in the dimer complex is greater than or equal to the time required for the complex to effect the desired cellular response. Polypeptide agonist variants of the ligand are identified by a method comprising (a) introducing a mutation into the ligand to produce an agonist candidate, (b) determining the affinity with which the candidate binds to the receptor through its first ligand site, (c), determining the affinity with which the candidate binds to the receptor through its second ligand site, and (d) selecting the candidate as an agonist if it binds at one or both of the first and second sites with greater affinity than the native ligand.

In accordance with this invention a method is provided for detecting an agonist or antagonist candidate for a polypeptide ligand, which ligand normally binds in sequential order first to a receptor polypeptide through a first ligand site and secondly to a second copy of the receptor polypeptide through a second ligand site different from the first site, comprising determining the effect of the candidate on the affinity of the polypeptide ligand for receptor at the ligand's second receptor binding site. Site 1 interactions are determined by immunoprecipitation using a site-2 blocking antibody such as Mab5 as described infra. Alternatively, the amount of wild type ligand that substantially forms only a 1:1 complex with receptor is determined and then the ability of the candidate to compete with native ligand for receptor at that proportion is determined. Site 2 interactions are assayed by following the ability of the candidate to form the ternary complex.

Where the candidate is a polypeptide analogue of the ligand then one positively correlates an absence of binding of the analogue at site 2 with antagonist activity. The ability to bind with greater affinity than native ligand to receptor site 2 is correlated with agonist activity. Antagonist and agonist activity are both positively correlated with the ability of the candidate to bind at site 1 with greater affinity than native ligand. Small molecule or other non-analogous candidates are assayed for their ability to promote or suppress binding of native ligand to sites 1 and/or 2. Antagonists are screened for their ability to interfere with native ligand-receptor binding at site 2 and/or site 1, but preferably site 2. This permits the identification of antagonists that do not suppress ligand receptor binding at site 1 but which do interfere with site 2 binding, using for example as a positive control a site 2 disabled variant of the ligand.

The effect of the candidate can be measured in the presence of the native polypeptide ligand or in comparison to the activity of the native polypeptide ligand. In the first alternative, the effect of the candidate on receptor interactions by the wild type ligand is measured. In the second the activity of the wild type ligand is used as a positive control and the receptor binding characteristics of the candidate (usually an amino acid sequence variant of the ligand) are measured without the presence of the wild type ligand. In general, however, the assays for agonist or antagonist candidates are best conducted as competition-type assays in the presence of wild type ligand.

We also have determined that selected antibodies capable of binding the GH receptor act as antagonists or agonists of GH. Accordingly, methods are provided for the antagonism or agonism of GH in the therapy of growth hormone deficiency or excess.

BRIEF DESCRIPTION OF THE DRAWINGS

FIG. 1a: Crystals of the complex between hGH and the hGHbp. The hGH/hGHbp complex was prepared by purifying the complex over a Sephadex G75–100 size exclusion column equilibrated in 10 mM Tris (pH 8.0) and 100 mM NaCl. The high molecular weight peak containing the complex was separated from free hGH, pooled and concentrated. The components were eluted isocratically (FIG. 1b) with a linear acetonitrile gradient at a flow rate of 1 ml/min. The gradient was started at the arrow and is illustrated with a dashed line; the absorbance at 214 nm is represented by the solid line.

Error bars give SEM.

Figure 11:
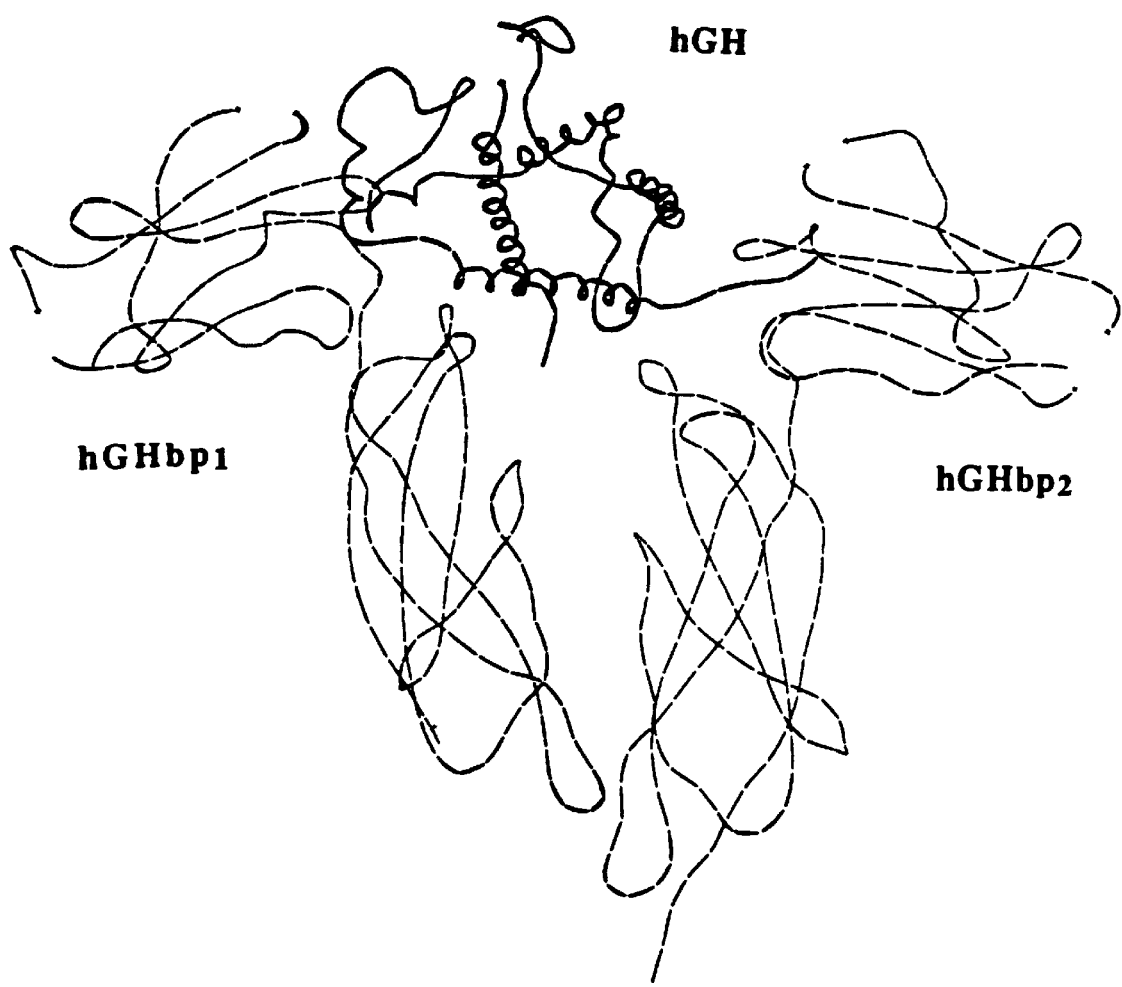

FIG. 11 Crystal Structure of $hGH(hGHbp)_2$. The central top region, in thicker lines, represents the hGH molecule. This hGH molecule is bound to two hGHbp molecules: one at the left hand side, and one at the right. Each of these hGHbp molecules has two domains linked by a single strand; the top domains are at the same height as the hGH molecule, the other domains are oriented vertically and stick out towards the bottom of the figure. These last two domains of the hGHbp contact each other at the very bottom.

Figure 12:
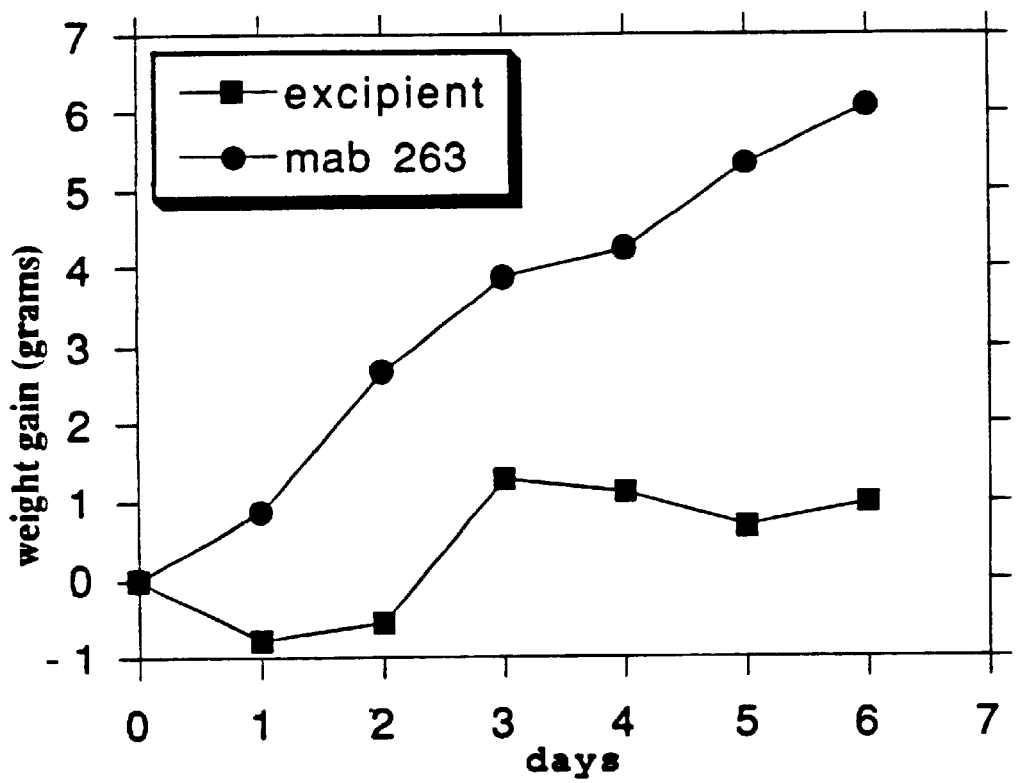

FIG. 12 Weight Gain in Response to Antibody Specific for Growth Hormone Receptor. Monoclonal antibody Mab 263, was administered (1.05 mg/kg) to eight rats, and the excipient alone administered to the control group. Daily weight measurments were taken.

Figure 13:
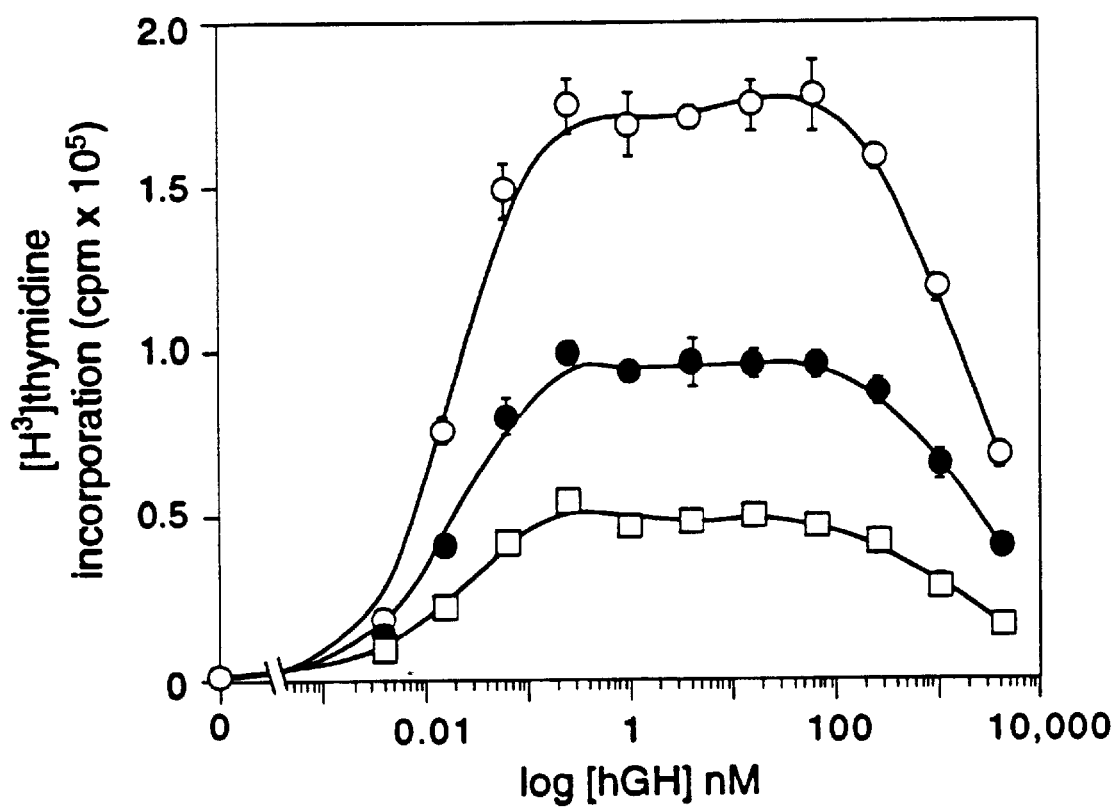

FIG. 13 hGH-induced proliferation of FDC-P1 cells containing the hGH-mG-CSF hybrid receptor (9). Cells were grown in RPMI 1640 media supplemented with 10 U/ml IL-3, 10 μM β-mercaptoethanol and 10% fetal bovine serum (FBS) at 37° C., 5% $CO_2$ (8). Cells were washed with same media without IL-3 and seeded in 96-well plates in 100 μl aliquots at a density of $4 \times 10^5$/ml (○), $2 \times 10^5$/ml (●), and $1 \times 10^5$/ml (□) prior to treatment with increasing concentrations of hGH for 18 h. To measure DNA synthesis cells were pulsed with [$^3$H]-thymidine by addition of 1 μCi/well in 20 μl media. After 4 h, cells were harvested and washed on glass filters. Two milliliters of scintillation cocktail were added and counted with Beckman LS1701 scintillation counter. Each data point represents the mean of triplicate determinations and error bars are the S.D.

Figure 14:
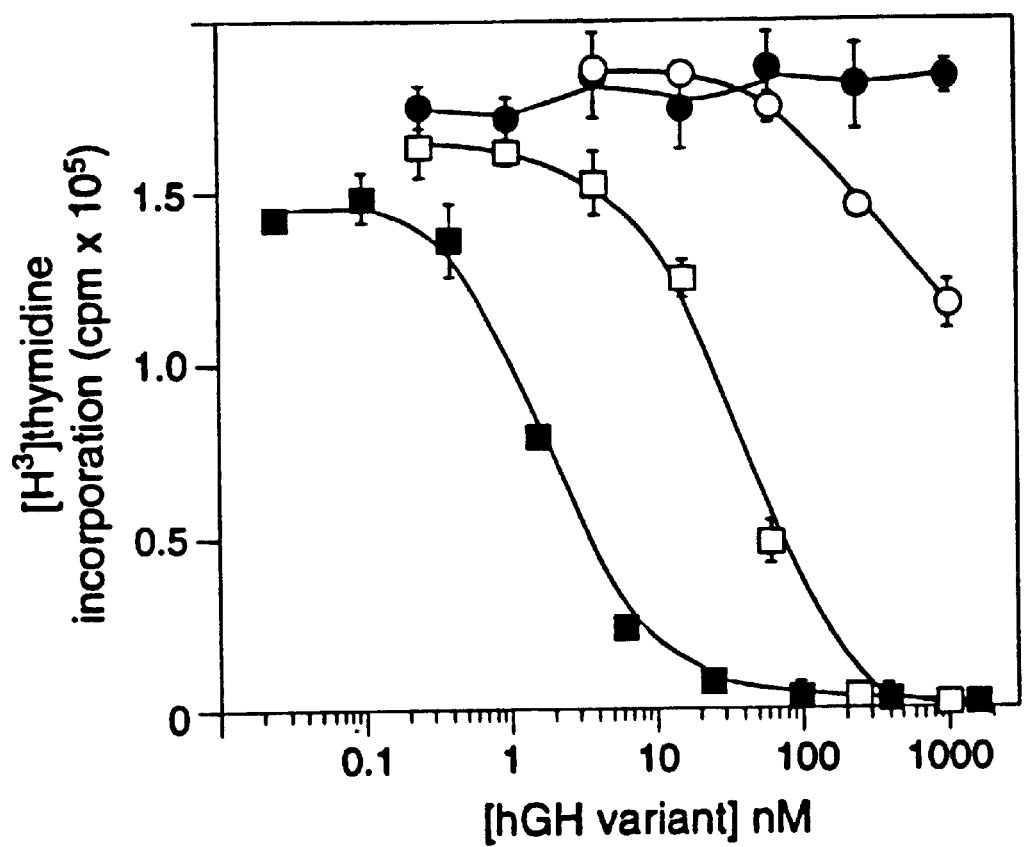

FIG. 14 Antagonism of hGH-induced cell proliferation by hGH variants. Cells were prepared as in FIG. 13 and incubated with 1 nM hGH plus increasing concentrations of the Site 1 mutant (K172A/F176A) (●), the Site 2 mutant (G120R) (□), the combined enhanced Site 1 mutant/Site 2 mutant (H21A/R64K/E174A/G120R) (■), and wild-type hGH (○).

Figure 15A:
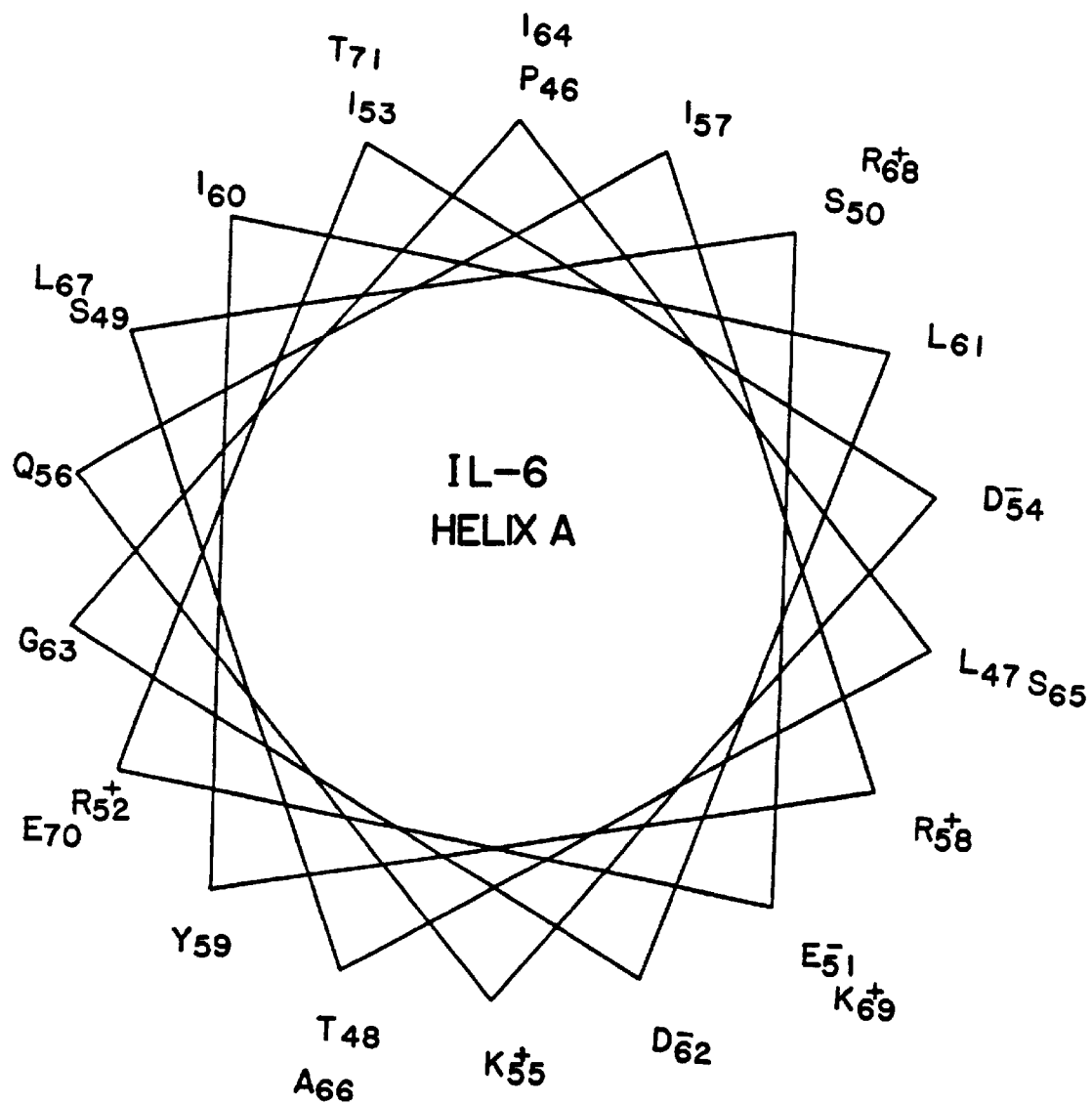
Figure 15B:
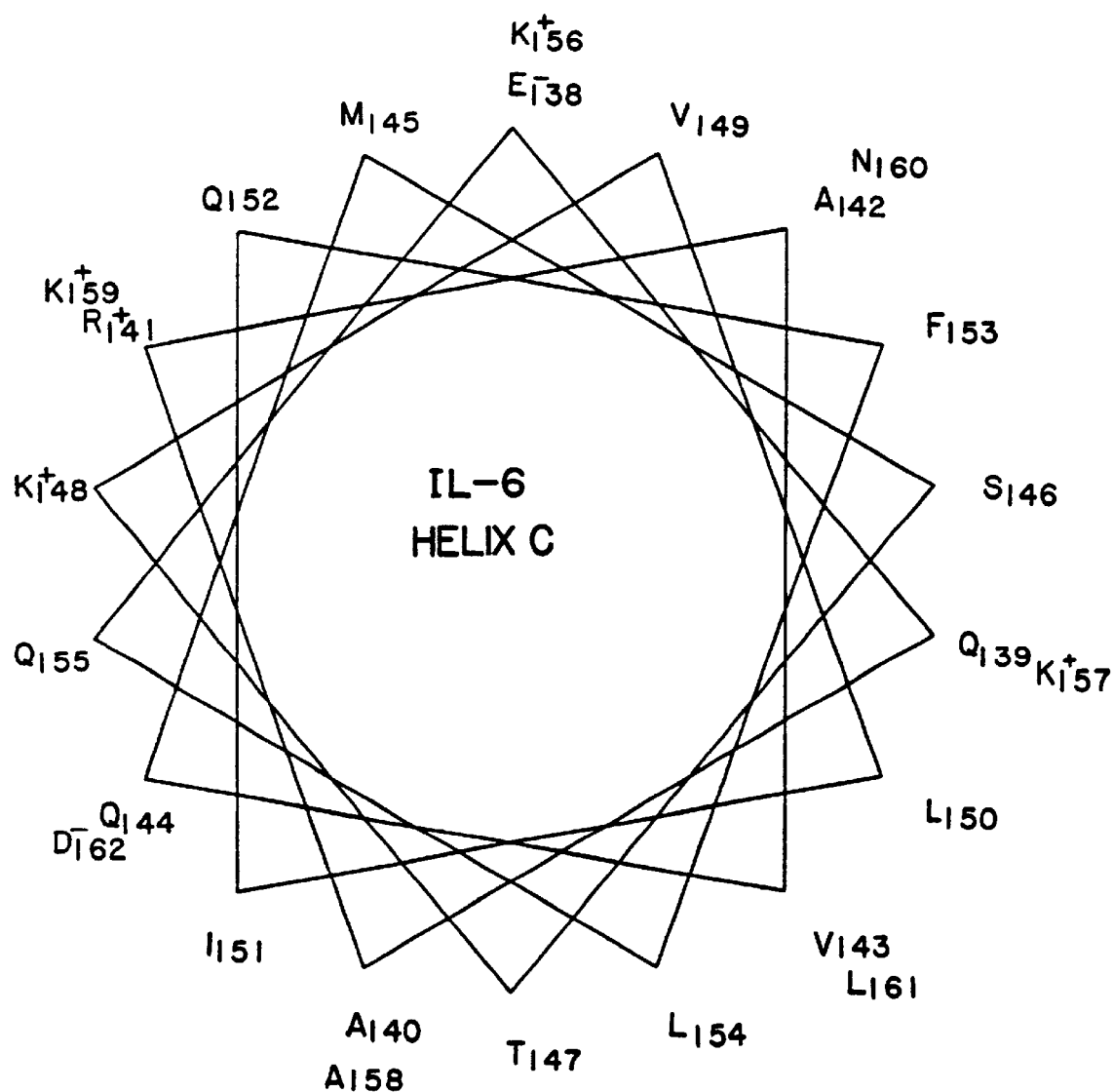
Figure 15C:
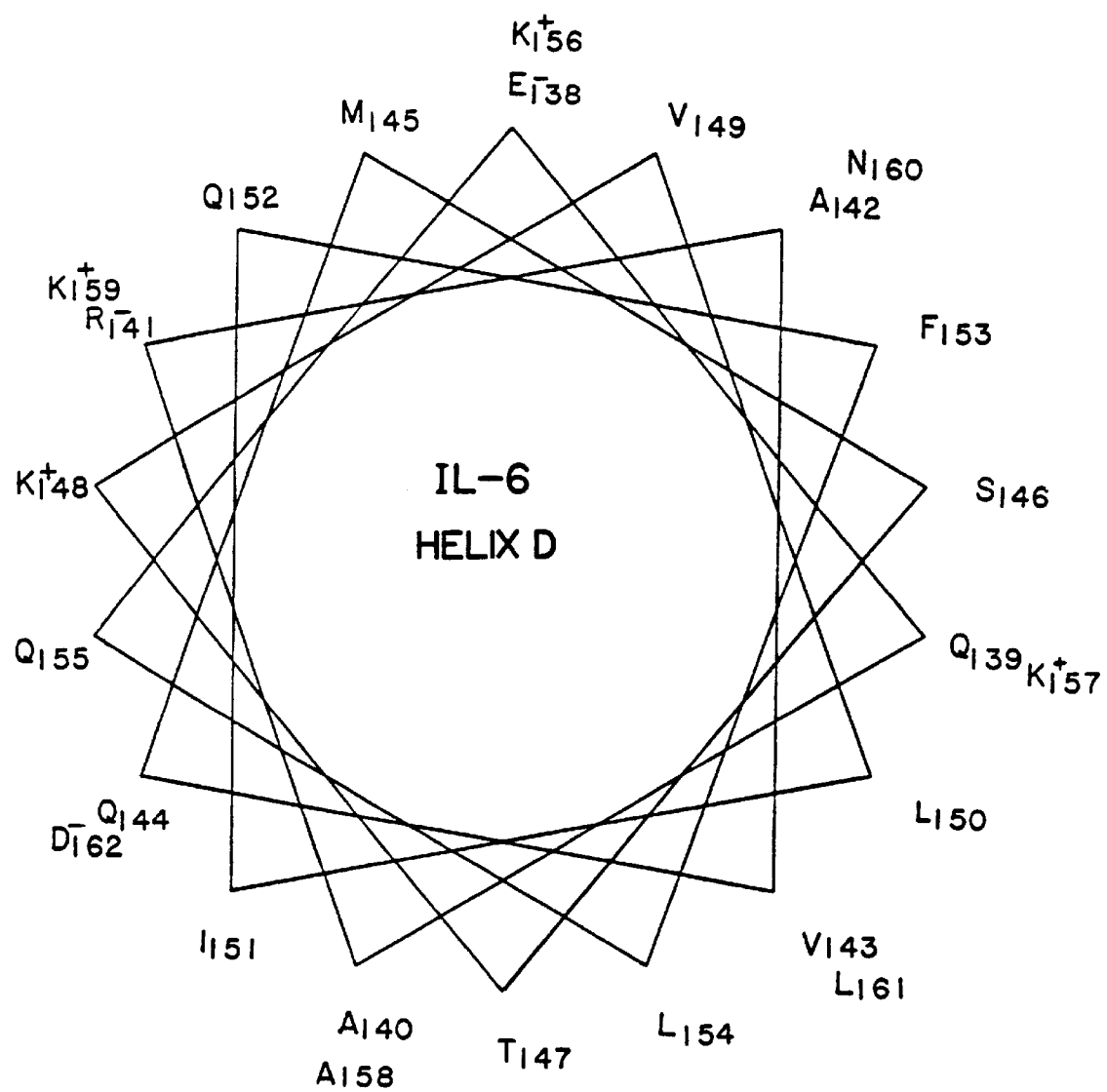

FIGS. 15a, 15b and 15c depict wheel plots of postulated α helical sites suitable for variation in preparing IL-6 antagonists or agonists. Note that residue numbering for these Figures commences with the N-terminal pre residue.

DESCRIPTION OF THE PREFERRED EMBODIMENTS

The method of this invention facilitates the identification of agonists or antagonists polypeptide ligands. In general, the method is practiced as follows.

First, one determines the stoichiometry of association of the ligand with its receptor in order to identify ligands that enter into 1:2 ternary complexes with their receptor. The stoichiometry of association is determined by measuring the proportion of ligand to receptor under physiological conditions using one of the methods set forth below, e.g., X-ray crystallography, size exclusion chromatography on Separose gels, antibody binding studies, scanning calorimetry, BIA-core analysis, and CD or fluorescence spectral analysis. It should be noted that an X-ray crystal structure of the ligand-receptor complex is useful but by no means required in order to determine the stoichiometry of description. Preferably, the fluorescein homoquenching method described further herein is used. In this method, the receptor is labelled with fluorescein positioned such that when two molecules of receptor are bound by ligand as determined by titration the fluorescein molecules quench one another and the fluorescence of the solution is decreases. The analytical techniques described herein are well known per se and within the skill of those in the art.

Preferably, the extracellular domain of the receptor is used in the stoichiometry analysis, i.e., the analysis is conducted in solution in vitro with receptor variants having their transmembrane domain deleted or otherwise rendered incapable of membrane insertion or hydrophobic association. Optionally, the cytoplasmic region also is deleted. Such receptors are known and can be expressed in and recovered from recombinant cell culture.

It the receptor contains more than one polypeptide chain then preferably the receptor preparation contains all of the receptor polypeptide chains. Also, if the ternary complex consists of two different receptor chains (as for example in the case of the IL-2 or IL-3 receptor complex containing alpha and beta chains, e.g., Teshigawa, et al., *J. Exp. Med.*, 165:223–238 [1978]) then the analysis is conducted with both chains. In this instance the binding to each receptor chain proceeds sequentially in one order only. The order of association is readily determined when different receptor molecules are involved.

Some receptors may form a 1:2 complex, but the receptors may each contain more than one chain. The use of multi-chain receptors may not be necessary if the ligand only binds to one of the chains and the other is not required for the maintenance of proper conformation of the binding chain; only the chains necessary for ligand binding need to be present.

Ligands forming 1:2 complexes bind to their receptors through two discrete binding sites. It is a significant feature of this invention that the receptors have been found to bind to these two sites in sequential order, first one site (site 1) and then the other (site 2). The reverse order has not been found to occur. This understanding is especially important for the preparation of antagonist ligands. It is important to preserve, if not enhance, the affinity of the ligand for the first site. Otherwise, the ligand analogue never binds receptor at all. On the other hand effective destruction or inhibition of the second site binding is predicate for antagonist activity.

In accordance with this invention the ligand binding sites and their order of addition are determined. Sites 1 and 2 are identified by comparing the conformation of the candidate ligand with that of growth hormone in the fashion more fully described below. They are more fully resolved by alanine scanning or other systematic mutagensis method, e.g., cassette mutagenesis, or PCR mutagenesis. Conformational analysis allows the field of potential sites 1 and 2 residues to be narrowed down considerably before making and screening variants.

In either case, a ligand analogue with a disabling site 2 mutation but functional site 1 is identified by its inability to form the ternary ligand:receptor complex although such a variant will be capable of forming a 1:1 complex with receptor. On the other hand an analogue with a disabling site 1 mutation but functional site 2 will be unable to bind to receptor at all. The assay employed for this determination is any assay that will detect association of polypeptides; the homoquenching assay described infra is acceptable, as is gel filtration and the like.

Conformation analysis facilitated the selection of ligand candidates from the class of amphipathic alpha-helical monomeric ligands. Since such ligands are conformationally related to growth hormones, placental lactogen and prolactin it is straight-forward to determine sites 1 and 2 for these ligands by analogy to the growth hormone structure. Ironically, the primary amino acid sequences of such ligands as EPO, alpha interferon, beta interferon, GM-CSF, G-CSF, and interleukins 2, 3, 4, 6 and 7 are poorly homologous to growth hormones, placental lactogen or prolactin. However, when these ligands (which generally are cytokines or hormones) are analyzed by conventional conformational structure principles (Bazan, et al., *Immunol. Today*, 11:350–354 (1991) Chou, et al.,*Biochemistry*, 13:222 [1974]); they are shown to exhibit certain common structural features. Most notably, they are characterized by 4 dominant amphipathic alpha helices, each preceded and followed by substantially non-helical structure (loops between helices and N- and C-terminal sequence at the protein terminii). The dominant alpha helices typically are about 15–30 residues in length. They are designated A–D, designated in order from the N-terminus. Short helical segments may be present in the loops joining dominant helices.

The alpha-helices of this class of ligands are amphipathic, i.e., they generally contain hydrophobic residues on one side of the helix and hydrophilic residues on the opposite side of the helix. Each 3.6 successive residues of the helix is termed a turn, in the sense of a spiral ladder. Some minor fraying in the terminii of the helices is to be expected, i.e., each alpha helical terminus may be varied by about 1–3 residues depending upon the algorithm employed and the discretion of the artisan. Despite the overall lack of homology among this group of ligands some conserved residues may be found in the helices and these can be used to assist in the structural alignment of the ligands with growth hormone.

Our analysis of growth hormone and the homologous ligands prolactin and placental lactogen demonstrated that site 2 for this group of quaternary-alpha helical cyokines and hormones principally is comprised by (a) the sequence extending from the N-terminus to about the first 3–4 turns of helix A and (b) about the middle 4–5 turns of helix C. Thus, site 2 is discontinuous but both segments are in close proximity in the protein and in that fashion interact with the receptor. Either or both site 2 domains are mutated. The helical hydrophobic residues generally are ignored for purposes of selecting candidate residues for mutagenesis, although occasionally they may affect the functional integrity of the candidate. In addition, not all residues within site 2 will exhibit functional or structural involvement in receptor binding. However, application of the principles herein greatly reduces the number of candidates that need to be screened for antagonist or agonist activity.

Antagonist variants are characterized by substantial changes in the charge, hydrophobicity or bulk of the native residue at the candidate location, as is more fully described below. This generally is accomplished by substituting the residue in question or by deleting it. In some instances the desired effect can be achieved by inserting a residue adjacent to a functionally or structurally active site 2 residue. The object tin the preparation of antagonists is to eliminate receptor binding at site 2, or to reduce it at least about 2 fold in relation to native ligand. This is most effectively accomplished by radically changing the character of one or more of the native residues that are important in structural interactions (hydrogen bonding, salt bridging, hydrophobic interactions and the like) with the receptor. Such residues are called structural residues. Alternatively, a residue is selected at a location, that does not directly contact receptor, but which is important in the proper positioning of a residue that does participate in a contact interaction. Such residues are termed functional residues.

Typically, no more than about 20 locations (residues) will be of potential interest in generating site 2 variants (excluding hydrophobic amphipathic residues). Of these, only a representative member of each amino acid group is employed in creating candidates, i.e., it is not ordinarily necessary to screen 19 variants, representing the remaining 19 naturally occuring residues, for each residue within site 2. Instead, representative members of residue groups are selected. Generally, these groups are (a) positively charged residues (K, R and H), (b) negatively charged residues (D and E), (c) amides (N and Q), (d) aromatics (F, Y and W), (e) hydrophobics (P, G, A, V, L, I and M) and (f) uncharged hydrophilic residues (S and T). Further, when preparing antagonist candidates, rather than screening 5 class-representative residues typically it is satisfactory to select only 1–3 classes because any substantial variation at the appropriate residue(s) will disable site 2. See Table 1a below. The most extreme substitutions are produced by selecting opposed combinations of features, e.g., if the native residue is alanine (small hydrophobic), then an extreme substituent would be glutamic acid, which is hydrophilic, bulky and charged. Further, residues are selected from those which show evolutionary diversity, i.e., if an animal species ligand fails to bind to human receptor site 2 then variant residues are selected as candidates. Thus, an adequate pool of mutants likely to contain an antagonist typically will contain about from 20 to about 60 site 2 variants. A slightly different strategy is used to select candidates for agonists at site 2. See the discussion below with respect to site 1. Producing and screening such pools would not involve undue experimentation and would be well within the ordinary skill in the art.

The selection of an amino acid for substitution also should take into account whether the residue is located within an alpha helix or a nonhelical structure. If the residue is part of a helical turn then the substituent preferably is not a helix breaker such as proline or glycine. On the other hand, if proline or glycine are the residues found in a wild type helix then they may be freely substituted since their substitution will not destabilize the helical conformation.

Site 1 also is a discontinuous site. It consists of three segments located (a) in the middle 40% of helix A (perhaps overlapping with the C-terminus of site 2 in helix A), (b) the C-terminal ⅔rds (preferably C-terminal ½) of the loop linking helices A and B, and (c) the C-terminal ½ (preferably ⅓) of helix D. The proportions refer to the linear sequence of amino acid residues. In contrast to the strategy to be used with site 2 antagonist mutations, the residues falling within the site 1 domains remain unmodified (in the case of antagonists, in which only site 2 is disabled by mutation) or, if modified, the changes to site 1 are selected so as to not disrupt binding. The reason is that it is not desirable in most embodiments to disable site 1. Instead, the objective is to increase site 1 affinity by about 10% to greater than 2 fold. Thus, residues within these domains generally are substituted (rather than deleted or subject to adjacent insertion), and the initial screen is with an alanine scan in order to identify hindrance determinants (residues whose bulky side chains, particularly when charged, hinder or inhibit the ligand-receptor binding interactions). Once hindrance residues are identified, site 1 substitutions for either agonists or antagonists are selected from Table 1a under the heading "agonist" substitutions. Species diversity analysis also will be helpful in identifying agonists as well. Again, no more than about 20 locations will need to be selected for site 1 variation. Generally at each location the mutation will be substitution with the remaining members of the original residue's group and the residues of the next most closely related group (Table 1a), which contain less bulky side chains and/or are unchanged.

TABLE 1a

Table of Candidate Substitutions Site 2

| Wild Type | Agonist | | Antagonist | |
|---|---|---|---|---|
| | Exemplary Group* | Preferred | Exemplary Group* | Preferred Group* |
| Ala (A) | e, f | S | a, b, c, d, | d |
| Arg (R) | a | K, S, A | b, d, e | b |
| Asn (N) | a, c, | Q, S, A | b, d, e | b |
| Asp (D) | b, c | E, S, A | a, d, e | a |
| Cys (C) | f, e | A, S | a, b, c, d | d |
| Gln (Q) | a, c | N, S, A | b, d, e | b |
| Glu (E) | b, c | D, S, A | a, d, e | a |
| Gly (G) | e, f | P, A | a, b, c, d | d |
| His (H) | a | E, R, S, A | b, d, e | b |
| Ile (I) | e | L, I, V, A | a, b, c, d, f | a, b, c |
| Leu (L) | e | I, L, V, A | a, b, c, d, f | a, b, c |
| lys (K) | a | R, S, A | b, d, e | b |
| Met (M) | e | L, I, V, A | a, b, c, d, f | a, b, c |
| Phe (F) | a, d | I, L, Y, V, A | b, c, e, f | f |
| Pro (P) | a, d | G, F, A | b, c, e, f | f |
| Ser (S) | a, f | A, T | a, b, c, d, e | d |
| Thr (T) | a, f | S, A | a, b, c, d, e | d |
| Trp (W) | d | F, A | a, b, c, e, f | a |
| Tyr (Y) | d | L, I, F, A, V | a, b, c, e, f | a |
| Val (V) | e | L, I, A, S | a, b, c, d, f | a, b, c |

*enumerated groups exclude designated wild-type residue; members of groups are listed above in the text.

Since each site contains several discontinuous domains variation is introduced into any one of the domains, i.e., it is not necessary to vary each domain of a given site. The helical domains of site 2 (helix A or C), preferably helix C, are the preferred mutagenesis locations for site 2. The helical domains of site 1 (helix A or D), preferably helix D, are the preferred locations for variation in site 1. Typically, only 1 residue is varied for each site, although it is within the scope of this invention to vary at least 1 residue in each domain of each site (2 for site 2, 3 for site 1). In other embodiments, 2 or more residues, usually up to about 5 residues, are varied at each domain.

Helical residue selection for mutagenesis or variation is facilitated by construction of helical wheel diagrams such as are shown in FIGS. 15a, b and c. These are prepared in conventional fashion and are useful in identifying target locations for variation in the helical portions of sites 1 and 2. Particular residues of interest are hydrophilic residues, non-bulky residues or residues that tend to destabilize the helical conformation.

While substitutions, insertions, deletions or combinations thereof are useful in preparing candidates for screening, the effect of the residue changes may extend beyond the residue changes per se. For example, a suitable method for modifying site 2 to prevent receptor binding is to introduce an N- or O-linked glycosylation site within site 2. The site will be glycosylated when expressed in yeast or higher eukaryotic cells, and will interfere with site 2 binding by steric hindrance. One advantage of this approach is that it is not necessary to determine the exact location of site 2 structural residues since insertion of a neighboring bulky group may be all that is required to inhibit binding. Other advantages are the ability to modulate, e.g., increase, the circulating half life and to reduce immunogenicity of the variant. Thus, for example, the invention includes the insertion of a glycosylation site in helices A and/or C (preferably C) of the ligands herein, e.g., IL-2.

The stable of candidate agonists or antagonists then is screened for the ability of the candidates to functionally act as agonists or antagonists. Such assays are conventional and widely available e.g., conventional assays typically used to assay potency and activity of the wild type ligand. Alternatively or in addition, the assays employed to determine receptor stoichiometry can be used (particularly to identify antagonists which bind at site 1 but not site 2). These assays per se are routine and do not require undue experimentation.

With respect to human growth hormone, site 2 contact residues include T3, I4, L6, L9, N12, L15, R16, R19, Q22, Y103, N109, D116, E119, G120, and T123. Site 2 functional residues include F1, I4, L6, R8, D116 and E119. Any residue is substituted at any one or more of these locations, the native residue is deleted or another residue is inserted adjacent thereto. As noted above, members of the same or different class are substituted, depending upon whether an antagonist or agonist affect is sought. Variation introduced into or adjacent to one or more of these locations will affect site 2 binding. In general, prefered residues for mutation include at least one mutation in the designated regions in the N-terminal domain/helix A and another in the C helix, especially F1, I4, L6, D119 and G120. Examples of hGH antagonists include I4A/L6A/G120A hGH, I4A/L6A/G120A/T123A hGH, F1A/I4A/G120I/T123A hGH, F1A/I4A/G120F hGH, and F1T/I4F/L6R/G120R/T123D hGH, as well as any of the foregoing with an additional mutation at a residue such as E174, H21, R64, K172, and/or F176 that increases the affinity of site 1 for its receptor. For example, E174 preferably is mutated to S, but also is mutated in other embodiments to a residue selected from G, V, L, I, A, T, D, N, Q, H, K, R, M, F, Y, W or P. F176 preferably is mutated to Y, and is optimally used in combination with E174S, R168N, D171S/A and/or I179T (from helix D) and, from helix A, F10A, M14W, H18D and H21N. Two site 1 hGH variants have been identified by phagemid screening that exhibit about 30 times tighter binding for the GHbp that does the wild type hormone: F10A/M14W/H18D/H21N/R167N/D171S or A/E174S/F176Y/I179T. Mutations at these sites are combined with the above-noted mutations at site 2 in order to produce agonists or antagonists. Examples of antagonists include F1A/I4A/F10A/M14W/H18D/H21N/G12OR, F, Y, W, D, E or I/R167N/D171S or A/E174S or A/F176Y/I179T hGH; F1A/I4A/H21A/R64K/E174A hGH, I4A/G120R/E174A hGH and I4A/G120I/E174A hGH.

In other antagonist embodiments, one or more residues selected from the group consisting of I4A, L6A, F1, and G120 are deleted while the remaining residues are substituted, and/or one or more residues are inserted adjacent to these residues. Combinations of substitutions, deletions and insertions are useful. Selecting them simply will be a matter of optimizing the activity of the growth hormone. Examples of such combinations include F1(Δ)/I4A/G120I/E174A, and I4(Δ)/G120(K)/E174A.

The effect of mutations at locations in sites 1 and 2 generally will be to depress binding and affinity, although selected modifications at these sites alternatively may lead to increases in affinity as determined by routine screening. For example, variation at E174 (S G, A or T) and at positions 21, 18 and 64 have been shown to increase site 1 affinity for GHbp.

HGH site 1 contact residues are H18, H21, Q22, F25, K41, Y42, L45, Q46, P61, S62, N63, R64, E66, R167, K168, D171, K172, T175, R178, and C189. Residues having side chains that affect the function of site 1 are P5, L6, F10, M14, F54, E56, I58, S62, N63, R64, E66, Q68, Y164, D171, K172, E174, T175, F176, R178, I179, C182 and V185. Preferred residues for increasing the affinity of site 1 for receptor are H21, R64 and E174. In general, site 1 residues are only substituted, and not deleted, nor are residues inserted adjacent thereto. Further, the site 1 substitutions generally will be drawn from the same group as the native residue or a closely related group, as noted in Table 1a; ordinarily it is not desirable to heavily perturb site 1 since both agonist and antagonist activity require that site 1 bind to receptor. Nonetheless, exceptions do exist, for example E174A, so it is desirable to screen a panel of substitutions to determine the optimal one.

Analogous residues in other growth hormones are easily identified and modified in the same fashion. For example, I4 in hGH corresponds to M4 in bGH. Note that some variation in residue numbers may exist in comparing growth hormones from other species as well as other alleles of hGH. If the animal GH does not contain the same residue as human GH at the homologous position then the substituted residue is one that is different from the animal residue and preferably different from human residue at that location. Otherwise, the selection of residues for mutagensis is conducted in the same fashion as described above.

Structural analysis or molecular modeling is used to identify analogous sequences for variation in other ligands, i.e., monomeric polypeptide ligands containing 4 antiparallel amphipathic alpha helices. The structure of the candidate ligand is determined using Chow Fassman analysis and then analogous residues located within sites 1 and 2 for each ligand are identified. In some instances, structural studies have already been published, and all that is needed is to compare the residues in the various domains with growth hormones in order to identify sites 1 and 2. Monomeric ligands are those which are found as monomers in circulation under normal physiological conditions.

Presently known examples of such ligands include EPO, GM-CSF, G-CSF, interleukins 2, 3, 4, 6 and 7, placental lactogen and prolactin, alpha-interferon, beta interferon. Others may be identified in the future and the teachings of this invention are equally applicable thereto.

In order to produce antagonist candidates for these ligands, substantial mutations are introduced into one or both of two regions: (a) from the N-terminus to the first N-terminal ⅓ of the A helix and (b) about the middle ½ (preferably ⅓) of the C helix. These domains correspond to the site 2 domain of hGH. Agonists are made by introducing less bulky and/or less charged substitutions into sites 1a and/or 2 (See Table 1). Optimal antagonists are produced by mutating site 2 to prevent or substantially delete receptor binding and by mutating site 1 to increase its affinity for receptor. As can be seen, site 1 is modified to increase its affinity for receptor in both the agonist and antagonist embodiment.

As an illustration of the manner in which antagonists and agonist variants of ligands other than growth hormone are prepared, reference is made to Table 1b below which discloses the postulated site 1 and 2 principal and core determinants for hPRL, IL-2, IL-3, IL-4, IL-6, GM-CSF, G-CSF and EPO. The helical determinants for each site were selected by identifying the helical domains of each ligand and comparing them with the analogous domains of hGH. The same analysis is applied in identifying non-helical domains that contribute to the structure or function of ligands other than hGH. Table 1b reflects our belief that antagonist variants preferably are made by targeting site 2 helical residues rather than site 2 domains in the N-terminii. However, non-helical analogous residues for sites 1 and 2 may also varied. The Table 1b residues postulated for sites 1 and 2 are believed to contain at least one residue that structurally or functionally interacts with the receptors for the tabulated ligands. This is readily confirmed by block alanine scanning or homolog-scanning of 1 to 3 of the 3 helical domains or portions thereof, deleting the domains or portions thereof, or substituting residues within one or more of the 3 domains so as to create an O- or N-linked glycosylation site. Once the activity of the domain is confirmed, it is a straight-forward matter to use residue-by-residue alanine-scanning to identify the key functional or structural residues.

TABLE 1b

Locations of helical segments and approximate sites 1 and 2 determinants in helices of various ligands.

| Hormone | Helix 1 | length | Site 2 | Helix 2 | Helix 3 | Length | Site 2 | Helix 4 | Length | Site 1 |
|---|---|---|---|---|---|---|---|---|---|---|
| hGH | 6–33* | (28) | 8–19 | 72–92 | 106–128 | (23) | 116–123 | 155–184 | (30) | 164–183 |
| hPRL | 15–42 | (29) | 17–28 | 79–104 | 114–138 | (25) | 125–132 | 162–193 | (32) | 172–192 |
| IL-2 | 12–27 | (18) | 13–20+ | 52–73 | 84–97 | (14) | 90–95+ | 115–133 | (19) | 121–133 |
| IL-3 | 18–27 | (10) | 19–23 | 56–66 | 69–81 | (13) | 75–79 | 105–120 | (16) | 110–119 |
| IL-4 | 5–17 | (13) | 6–11 | 40–56 | 72–90 | (19) | 81–87 | 110–125 | (16) | 115–124 |
| IL-6 | 18–43 | (26) | 20–30 | 80–102 | 110–134 | (25) | 121–130 | 154–184 | (31) | 163–183 |
| GM-CSF | 13–28 | (16) | 14–21 | 55–64 | 74–87 | (14) | 80–85 | 103–116 | (14) | 108–115 |
| G-CSF | 10–35 | (26) | 12–22 | 73–96 | 105–127 | (23) | 116–123 | 148–176 | (29) | 157–175 |
| KPO | 4–28 | (25) | 6–16 | 58–82 | 89–113 | (25) | 101–109 | 136–160 | (27) | 145–159 |

*Residues numbered from first N-terminal mature residue
+Site 2 for IL-2 is believed to bind to the IL-2 receptor beta chain. Antagonists are conveniently assayed by forming a 1:1 complex of IL-2 candidate with IL-2 receptor alpha chain and screening for the ability of the 1:1 complex to bind beta chain. Similarly, site 1 agonists are identified by screening for their ability to compete with native IL-2 for the receptor alpha chain.

Helix structural information for Table 1b was obtained from DeVos, et al., *Science*, 225:306–312 (1992)(hGH); Bazan, et al., *Immunol. Today*, 11:350–354 (1991) (hPRL, IL-6, IL-2 and EPO); Lokker, et al., *EMBO J.*, 10:2125–2131 (1991); Bazan, et al., pp cit. (IL-2); and Diederichs, et al., *Science* 254:1779–1782 (GM-CSF). As noted above, such information for other ligands if obtained by modeling, nmr, or preferably, by x-ray crystallographic analysis.

The site designations in Table 1b were arrived at by calculating contact patches based on site 2 being 0.07 to 0.5 of the length of helix A and 0.5 to 0.8 of the length of helix C. These sites should be considered approximate and likely will require modest refinement; each site may be positioned ±1–5 residues from the sequence noted.

In the preparation of antagonists the residues or structures introduced into the target helical residues generally are not of the same class (see supra) and preferably are more bulky than the residue for which they are substituted. In other embodiments, the site residues are deleted, or other residues (such as helix breakers like G or P) are inserted adjacent to a site residue. A group of candidates then are prepared and screened by the methods set forth herein to identify optimal candidates. It should be emphasized, however, that even if a variant ligand fails to act as an agonist or antagonist in comparison with native ligand, the variant is useful for the conventional uses for the ligand (where the variant retains approximately the same activity as the native ligand) or as an immunological, e.g., diagnostic, reagent where it is unable to bind to receptor.

A representative scheme for preparation of IL-2 antagonist candidates is shown in Table 1c. In this scheme, putative site 2 residues as identified in Table 1b are substituted with preferred amino acids for reduced receptor binding. Addtional alternative substitutions are also indicated in the Table.

TABLE 1c

Substitutional Mutations for Production of IL-2 Antagonist Candidates

| Residue | Wild-type | Preferred Substitutions | Alternative Substitutions |
|---|---|---|---|
| 13 | Q | A, R | N, D, B, C, E, Z, G, H, I, L, M, F, P, S, T, W, Y, V |
| 14 | L | A | R, N, D, B, C, Q, E, Z, G, H, I, K, M, F, P, S, W, Y, V |
| 15 | E | A, R | N, D, B, C, Q, Z, G, H, I, L, M, F, P, S, T, W, Y, V |

TABLE 1c-continued

Substitutional Mutations for Production of IL-2 Antagonist Candidates

| Residue | Wild-type | Preferred Substitutions | Alternative Substitutions |
|---|---|---|---|
| 16 | H | A, R | N, B, C, Q, E, Z, G, I, L, K, M, F, P, S, T, W, Y, V |
| 17 | L | A, R | D, B, C, Q, E, Z, G, H, I, K, M, F, P, S, T, W, Y |
| 18 | L | A | R, N, D, B, C, Q, E, Z, G, H, I, K, M, F, P, S, W, Y, V |
| 19 | L | A | R, N, D, B, C, Q, E, Z, G, H, I, K, M, F, P, S, W, Y, V |
| 20 | D | A, R | N, B, C, Q, Z, G, H, I, L, K, M, F, P, S, T, W, Y, V |
| 90 | N | A, R | D, B, C, Q, E, Z, G, H, I, L, K, M, F, P, S, T, W, Y, V |
| 91 | V | A, W | R, N, D, B, C, Q, E, Z, G, H, I, L, K, M, F, P, S, T, Y |
| 92 | I | A, W | R, N, D, B, C, Q, E, Z, G, H, L, K, M, F, P, S, T, Y, V |
| 93 | V | A, W | R, N, D, B, C, Q, E, Z, G, H, I, L, K, M, F, P, S, T, Y |
| 94 | L | A, W | R, N, D, B, C, Q, E, Z, G, H, I, K, M, F, P, S, T, Y, V |
| 95 | E | A, R | N, D, B, C, Q, Z, G, H, I, L, K, M, F, P, S, T, W, Y, V |

Representative helical wheel plots for IL-6 helices A, C and D are depicted in FIGS. 15a, b and c, respectively. Of potential interest in helix A are D54, R58, E51, K55, T48, R52, Q56 and S49, and in helix C are K157, A158, Q155, Q152, K156 and V149.

A similar plot for hPRL suggests that locations for modifying site 2 are residues H58, D69, H55, D48, N59, V52, D45, Y56 and R49 (helix A) and K143, Q150, G157, E146, Q164, R153, L160, S142, E149, S163, V145, K152, E148, H166, E156 and E159 (helix C).

hPRL site 1 (helix D) residues of interest are C202, R220, S191, K209, N198, L216, R205, S194, N212, H201, C219, E190, H208, Y197, K215, R204, D211, L193, L200 and K218. hPRL residues are numbered with the N-terminal M of the presequence=1.

Of course, the agonists and antagonists herein also include ligands in which variation is introduced into additional residues than those found in sites 1 and/or 2. For example, the candidates are fused to other polypeptides, e.g., to facilitate immunoaffinity purification, have regions or residues deleted, substituted or inserted which do not participate in the desired activity and are not required for maintenance of the proper conformation, e.g., to make active fragments of the ligands, or otherwise are varied in accord with conventional practice.

The Ka, or affinity constant, with which the ligand binds to receptor is the ratio of the rate at which the ligand binds to receptor (the "on" rate) divided by the rate at which the ligand disassociates from the receptor at the site in question (the "off" rate). A high affinity interaction is one in which the "on" rate predominates. Antagonists generally will have high affinity variation at site 1. For the most part a high affinity variant at either site is desirable for agonists depending on the nature of the receptor. If the ligand binds to the receptor and the ternary receptor complex issues a single rather than continuous signal, a ligand analogue having an extremely high affinity for receptor may in fact occupy receptor for so long that it, in effect, begins to act as an antagonist. For example, if 20–30 minutes are required for the dimerized receptor to signal a change in the character of the cell (e.g., releasing protein, stimulating mitosis, etc.), then it would be unnecessary for an agonist ligand to possess a rate constant whereby in occupies the receptor for a matter of hours. Thus, the agonist affinity optimally should be optimized so that the variant dissociates from the receptor after approximately the same period as is required to complete the receptor signalling event. A high (>fold over wild type) site 1 Ka is entirely desirable for an antagonist having an inactive site 2 since this would enhance the occupation of receptor site 1 by the antagonist and thereby tie up receptor that otherwise might become available to native ligand. Thus, agonist mutations most desirably will have rate constants consistent with the signalling character of the dimerized receptor, while antagonists will exhibit high affinity at site one and lower (or absent) affinity at site two. Ka is readily determined for a given ligand variant, for example by use of BIA-core equipment which is commercially available from Pharmacia.

The ability of ligand and its receptor to form ternary complex also serves as a convenient assay endpoint for substances that influence the formation of the complex but which are not ligand amino acid sequence variants. For example, if one desired to screen a group of candidate non-peptidyl or short peptide molecules for agonist or antagonist effect one need only follow the formation of the ternary complex in the presence and in the absence of the candidate. Candidates that suppress complex formation will act as antagonists; those that reduce the quantity of ligand and receptor required to form the complex will be agonist candidates. Non-specific effects on the receptor or ligand, e.g. protein denaturation, are excluded by conventional analysis, e.g. CD studies.

Similarly, the assay method is useful to detect variant receptors and their activity. For example, a mutant receptor is assayed for its ability to bind correctly to ligand by measuring its ability to compete with native receptor for a ligand binding site. In such an assay using homoquenching, fluorescein labeled receptor is added to a limiting amount of native ligand, and the ability of the candidate receptor to compete with labeled receptor is measured by increased fluorescence in relation to receptor standard. Fluorescence quenching or enhancement also can be detected by labeling half of the receptor population with one fluorophore and the other half with the enhancing or quenching molecule. Such systems are widely known and are generally applicable to the ternary assay. The assay also can be adapted to permit analysis of site 1 or site 2 binding by simply following the molecular size of the complex. If the ligand and receptor do not form any complex at all, despite adequate proportions, then site 1 is deficient, or (when receptor is the candidate) the receptor binding site for ligand site 1 is deficient. If only a 1:1 complex is formed (even though adequate amounts of ligand or receptor are present) then ligand site 2 (or its receptor site, depending upon the candidate used) is deficient in its ability to bind to receptor. The same analysis is applied to identifying ligands or receptors that are capable of binding at site 1 or 2 with greater affinity than the wild type protein.

Assay for Complex Formation

Assay methods for detection of the ternary complex include determining the molecular weight of the complex, determining fluorescence emission or fluorescence quenching or other energy transfer between labels on the receptor, Bia-core analysis, gel exclusion chromatography, native gel electrophoresis, isoelectric focusing, sedimentation and dialysis. Other suitable methods include the use of antibodies binding to the receptor-ligand sites, optical rotation of polarized light, chromatography, and nuclear magnetic resonance. Among the types of chromotography are gel filtration, ion exchange and high pressure liquid chromatography (HPLC). Any method of analysis will work that allows a determination of the ternary complex formation against a background of the uncomplexed ligand and/or receptor.

Ligands and their Receptors

Included among the ligands which are structurally analyzed and, if appropriate, mutated in accord herewith are growth hormones, insulin-like growth factors, parathyroid hormone, insulin, relaxin, glycoprotein hormones such as follicle stimulating hormone (FSH), thyroid stimulating hormone (TSH), and leutinizing hormone(LH), hemopoietic growth factor, hepatic growth factor, fibroblast growth factor, prolactin, placental lactogen, tumor necrosis factor-alpha and -beta, mullerian-inhibiting substance, mouse gonadotropin-associated peptide, inhibin, activin, vascular endothelial growth factor, integrins, thrombopoietin, nerve growth factors such as NGF-β, platelet-derived growth factor, transforming growth factors (TGF) such as TGF-alpha and TGF-beta, insulin-like growth factor-I and -II, EPO, osteoinductive factors, interferons such as interferon-alpha, -beta, and -gamma, colony stimulating factors (CSFs) such as M-CSF, GM-CSF, and G-CSF, interleukins (ILs) such as IL-1, IL-2, IL-3, IL-4, IL-5, IL-6, IL-7, IL-8 and other polypeptide factors. Preferred ligands are helical monomeric cytokines/hormones such as G-CSF, GM-CSF, Il-2, IL-3, IL-4, IL-6, IL-7, EPO, growth hormone, placental lactogen and prolactin. Receptors for these ligands are used in the same fashion as for hGH and antagonists or agonist are selected as described above.

The foregoing discussion has concentrated on amino acid sequence variation. However, the same objectives also are accomplished by convalently modifying the target residues (s) by in vitro methods. This may be effected through any type of chemical modification which disrupts or modifies the ability of the side chains of the residues at the target locations to bind to receptor. The net effect is the same, e.g., as substitutional mutations provided the covalent modification is sufficiently specific for the target residue(s). Specificity is achieved by selecting agents which react preferentially with the desired side chain; additional specificity is achieved by blocking other side chains with antibodies which bind to the regions to be protected. The modification may be of one or more of the amino acids that directly participate in the binding (structural residues); alternatively amino acids adjacent or in the region of receptor binding which are involved in maintenance of conformation are covalently modified in vitro. The covalent modification includes such reactions as oxidation, reduction, amidation, deamidation, condensation and so forth, or substitution of bulky groups such as polysaccharides or polyethyleneglycol. Methods for covalently attaching such moieties (e.g., polyethyleneglycol) to proteins are well known (see for example Davis, et al. U.S. Pat. No. 4,179,337).

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate, and N-hydroxysuccinamide esters of polyethylenene glycol or other bulky substitutions.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'-N=C=N-R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco, pp. 79–86 [1983]), acetylation of the N-terminal amine, and amidation of any C-terminal carboxyl group.

Evidence for two binding sites on the hGH comes from antibody binding. The affinity of hGH for the hGHbp is measured by displacement of [$^{125}I$]hGH from the hGHbp and precipitating the complex with an anti-receptor monoclonal antibody (Mab5) produced from glycosylated rabbit GH receptor (Barnard, R. et al., *Endocrinology* 115:1805–1813 (1984); Barnard, R. et al., *Biochem. J.* 231:459–468 (1985)). Using this assay, Scatchard analysis shows that hGH and the hGHbp form a 1:1 complex (Leung, D. W. et al., *Nature* 330:537 (1987); Fuh, G. et al., *J. Biol Chem.* 265:3111–3115 (1990) Barnard, R. et al., *Endocrinology* 115:1805–1813 (1984); Barnard, R. et al., *Biochem. J.* 231:459–468 (1985); Spencer, S. A., et al., *J. Biol. Chem.*, 263:7862–7867 (1988)). Scatchard analysis of displacement curves (FIG. 3), using another set of MAbs (MAb387 or 3D7), produced stoichiometries of 0.5 hGH to 1 hGHbp. These results can be explained if Mab5 were to block determinants on the hGHbp for binding to a second site on hGH.

Evidence for two binding sites on each hGH polypeptide was developed using monoclonal antibodies in the scanning-mutational analysis of binding determinants between hGH (Cunningham, B. C. et al., *Science*, 244:1081 (1989)) and the hGHbp (Example 2). The determinants identified in these studies are important for modulating formation of the 1:1 complex. Based upon this data we installed these determinants into non-binding homologs of hGH and created analogs that bind tightly to the hGHbp (Cunningham, B. C., et al., *Science*, 247:1461–1465 (1990)). By incorporating 8 substitutions into hPRL or 5 into hPL, we have produced variants that bind to the hGHbp and form a 1:1 complex.

We used gel filtration to determine if these hPRL or PL variants could bind to one or two molecules of the hGHbp. At a 2:1 ratio of hGHbp to hormone, both binding variants of hPRL show two symmetrical peaks corresponding to a 1:1 complex with the hGHbp.

Figure 5:
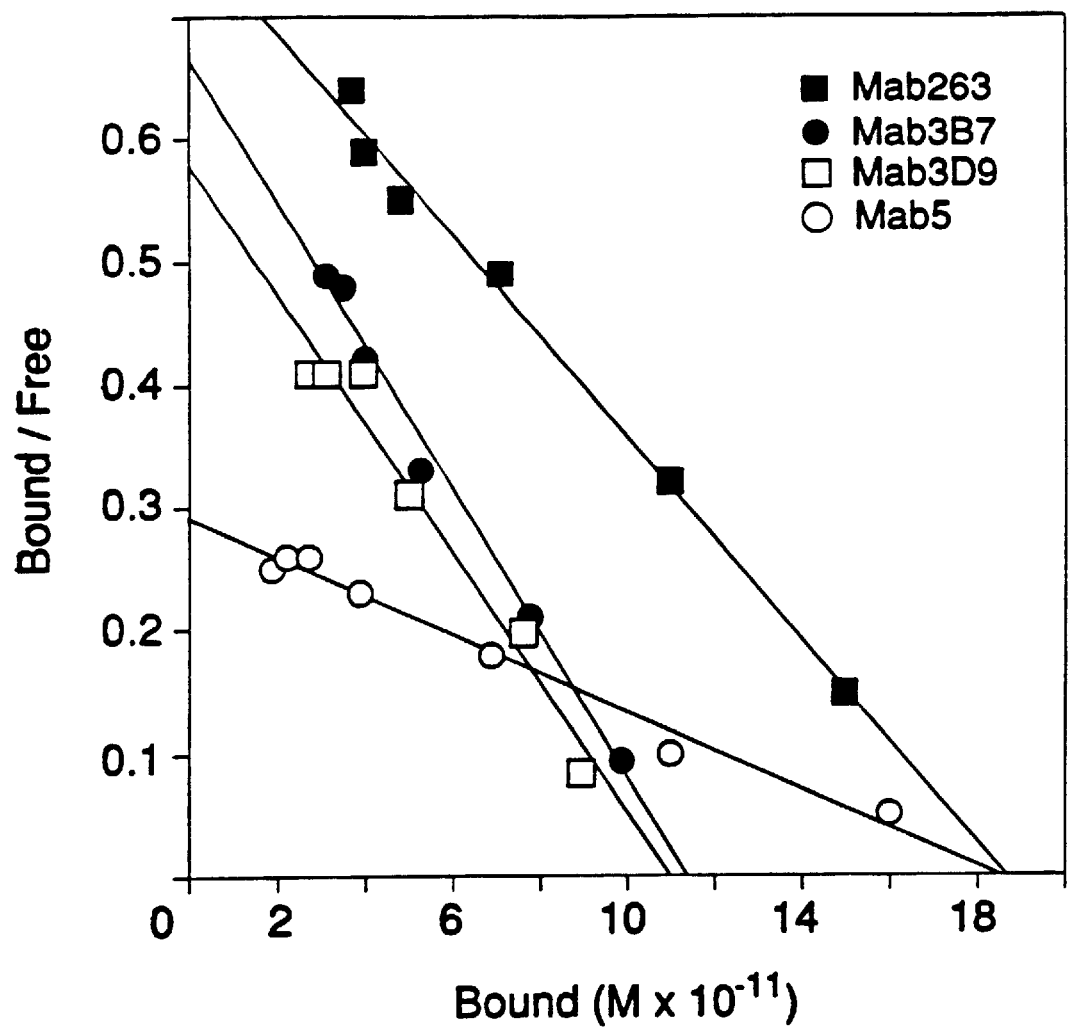
FIG. 5. Scatchard analysis for binding of hGH to the hGHbp where complexes were precipitated with various anti-hGHbp monoclonal antibodies.

We employed scanning calorimetry to further evaluate the stoichiometry and heat of reaction because binding can be studied free in solution without the need to employ antibodies or chromatography to separate complexes (FIG. 5). This experiment allowed us to determine the equivalents of hGH bound to the hGHbp and the heat of reaction.

In Table 1d we summarize the titration end points for wild-type hGH and variants of hGH and hPRL. The ratio of hGH necessary to bind to all of the hGHbp is about 0.5 to 1. Altogether these data strongly indicate that the hPRL and hPL variants are missing important determinants for dimerization of the hGHbp. These determinants are largely conserved in the single alanine mutants of hGH but not in the hPRL or hPL variants. This suggests there are two binding sites on hGH for the hGHbp. One of these sites has been functionally characterized in detail by alanine-scanning mutagenesis of hGH (Cunningham B. C. et al., *Science*, 244:1081 (1989)) or the hGHbp using the Mab5 or Mab263 immunoprecipitation assay, respectively. The second sites on hGH and the hGHbp remained to be elucidated.

Figure 6A:
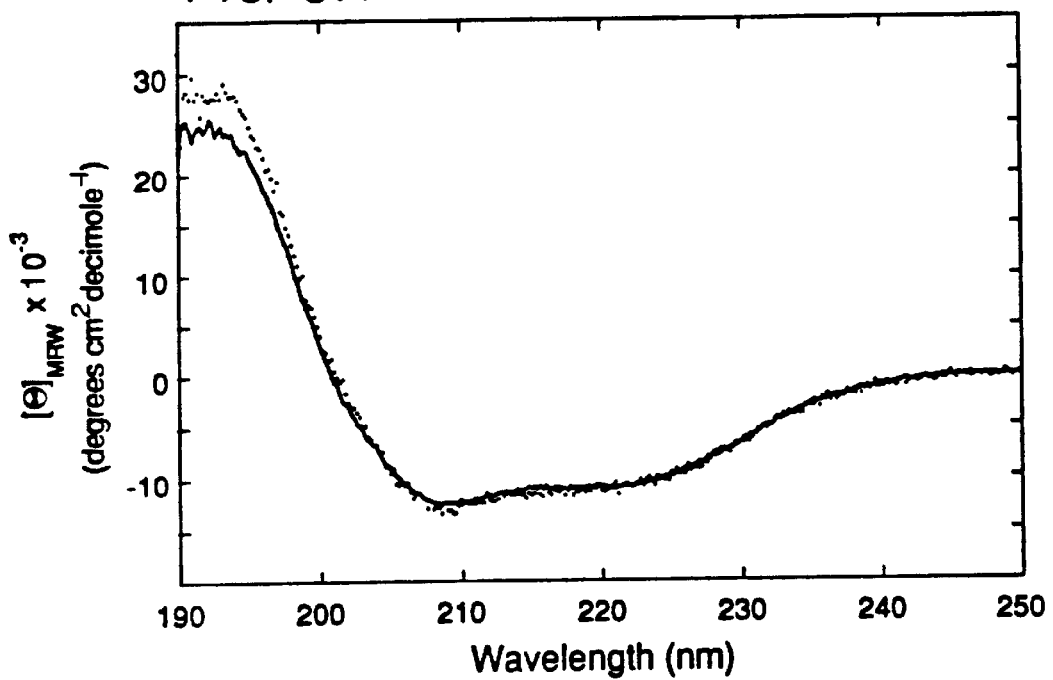
FIG. 6. Circular dichroic spectra in the far UV (FIG. 6A) or near UV (FIG. 6B) of the sum of the individual spectra of hGH and the hGHbp before (–) and after ( . . . ) mixing the two at a 1:1 ratio. Far-UV and near-UV spectra were collected at 0.2 nm and 0.5 nm intervals in 0.01 cm and 1.0 cm cells, respectively.
Figure 6B:
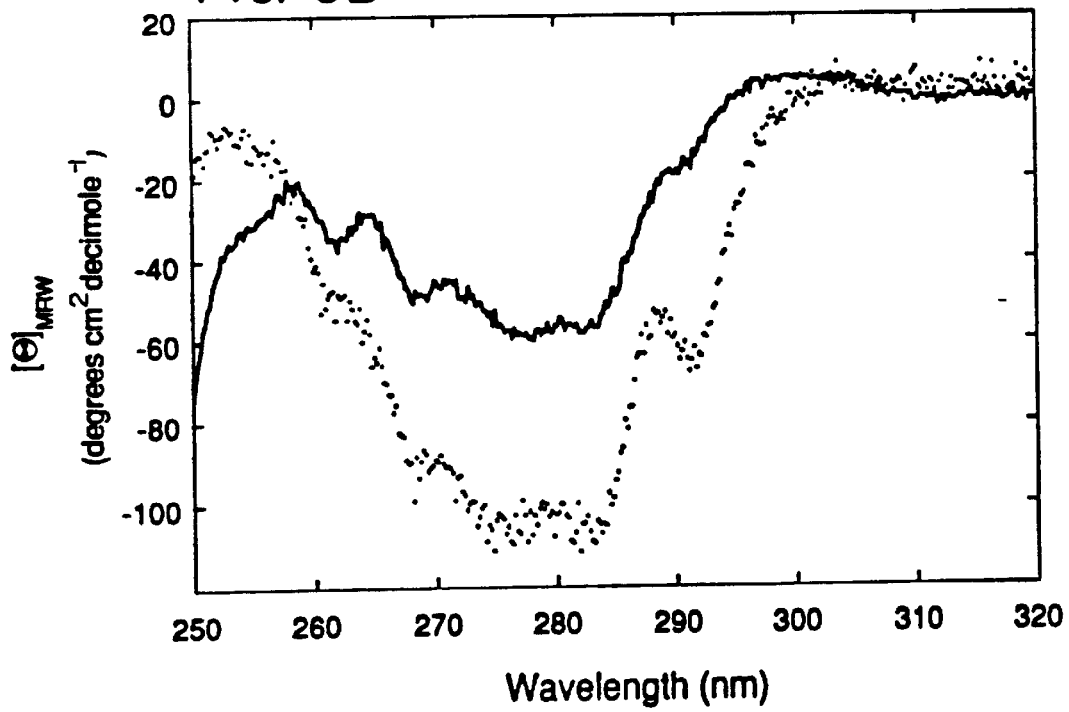

Binding of hGH to the hGHbp causes little spectral change in the components. We investigated the change in the circular dichroic (CD) and fluorescence spectra upon complex formation. When hGH and the hGHbp are mixed the far UV CD spectrum is virtually identical to the sum of the spectra of hGH and hGHbp (FIG. 6A). This result indicates the absence of large changes in regular secondary structure upon formation of the complex. The near UV CD spectrum (FIG. 6B) reflects the asymmetric environment of the aromatic amino acid side chains (Bewley, T. A. *Recent Progress in Hormone Research*, 35:1555 (1979); Bewley T. A. et al., *Archives of Biochemistry and Biophysics*, 233:219–227 (1984)). There are large differences between the UV absorbance spectra of hGH and the hGHbp, largely a result of the greater tryptophan content of the hGHbp compared to hGH (9 versus 1, respectively). However, except for an increase in the intensity of the spectrum the sum of the individual spectra are essentially identical to that obtained after mixing.

Figure 7:
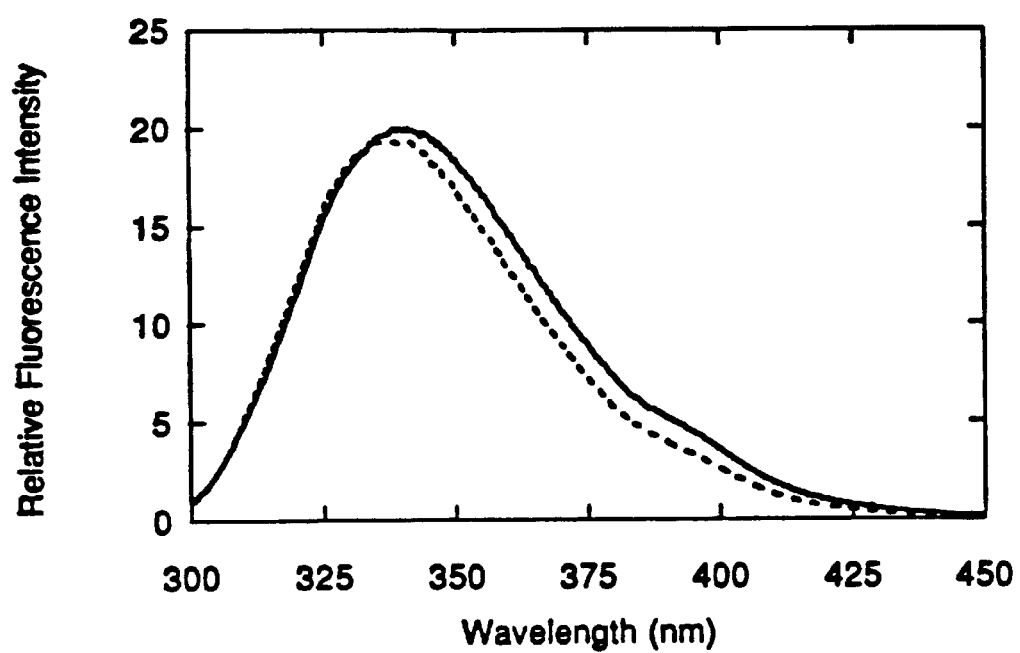
FIG. 7. Fluorescence emission spectrum of the sum of the individual spectra of hGH and hGHbp before (–) and after ( . . . ) mixing the two at a 1:1 ratio.

In the fluorescence spectrum, there is a blue shift from 340 nanometers to 334 nanometers and slight reduction in the fluorescence intensity upon hGH binding to the hGHbp (FIG. 7). Iodide quenching and Stem-Volmer analysis indicate there is a reduction in the exposure of tryptophan in the hormone receptor complex. This is likely the result of burying one or more Trp residues in the hGHbp upon binding hGH because fluorescence quenching studies have shown that the tryptophan in hGH is not appreciably exposed to solvent (Bewley, T. A., *Recent Progress in Hormone Research*, 35:1555 (1979); Bewley, T. A. et al., *Archives of Biochemistry and Biophysics*, 233:219–227 (1984)). In contrast, mutational analyses of the hGHbp show that Trp104 is especially important in binding to hGH.

As discussed above, the hGH results are relevant to other polypeptide ligands, e.g., hormone-receptor and cytokine-receptor systems. The growth hormone and prolactin receptors appear to be structurally related to a large family of cytokine receptors for interleukin 2, 3, 4, 5, 6, 7, erythropoetin, macrophage colony stimulating factor and others (for reviews see 8). It is striking that the intracellular domains of these receptors share little if any sequence homology, and none appear homologous to any known tyrosine kinase. Nonetheless, the GH (Carter-Su, C., et al., *J. Biol. Chem.*, 264:18654–18661 (1989)), IL-2 (Asao, H., et al., *J. Exp. Med.* 171:637–644 (1990)), and IL-3 (Itoh N., et al., *Science* 247:24–327 (1990)) receptors become phosphorylated shortly after hormone binding. In the case of the IL-2 (Sharon, M. et al., *Proc. Natl. Acad. Sci. USA* 87:4869–4873 (1990)) and IL-6 (Taga, T., et al.,*Cell* 58, 573–581 (1989)) receptors there is evidence indicating that accessory proteins and/or receptors are involved in signal transduction. The present results with hGH and its binding protein, support a model for activation of the hGH receptor in which hGH binding induces dimerization of the extracellular portion of the receptor which brings together the intracellular domains to create an active domain that may interact with cytoplasmic (or membrane bound) components. This may or may not occur without substantial change in conformation of the complexed components.

Two other groups have recently crystallized a polypeptide hormone in complex with its extracellular binding domain (Lambert, G., et al.,*J. Biol Chem.* 264:12730–12736 (1989); Gunther, N., et al.,*J. Biol. Chem.* 265:22082–22085 (1990)); however neither reports conclusive evidence for receptor dimerization. Human IL-2 was crystallized predominantly in a 1:1 complex with a soluble recombinant form of the human p55 component of the IL-2 receptor, although a small amount of disulfide linked p55 dimer was observed. Cross-linking studies suggest that the functional IL-2 receptor complex is a heterodimer formed between IL-2, p55 and another receptor component called p70 (Saragori H., et al., *J. Immunol.* 139:1918–1926 (1987); Ogura, T., et al., *Mol. Biol. Med.* 5:123–138 (1988)).

Figure 2:
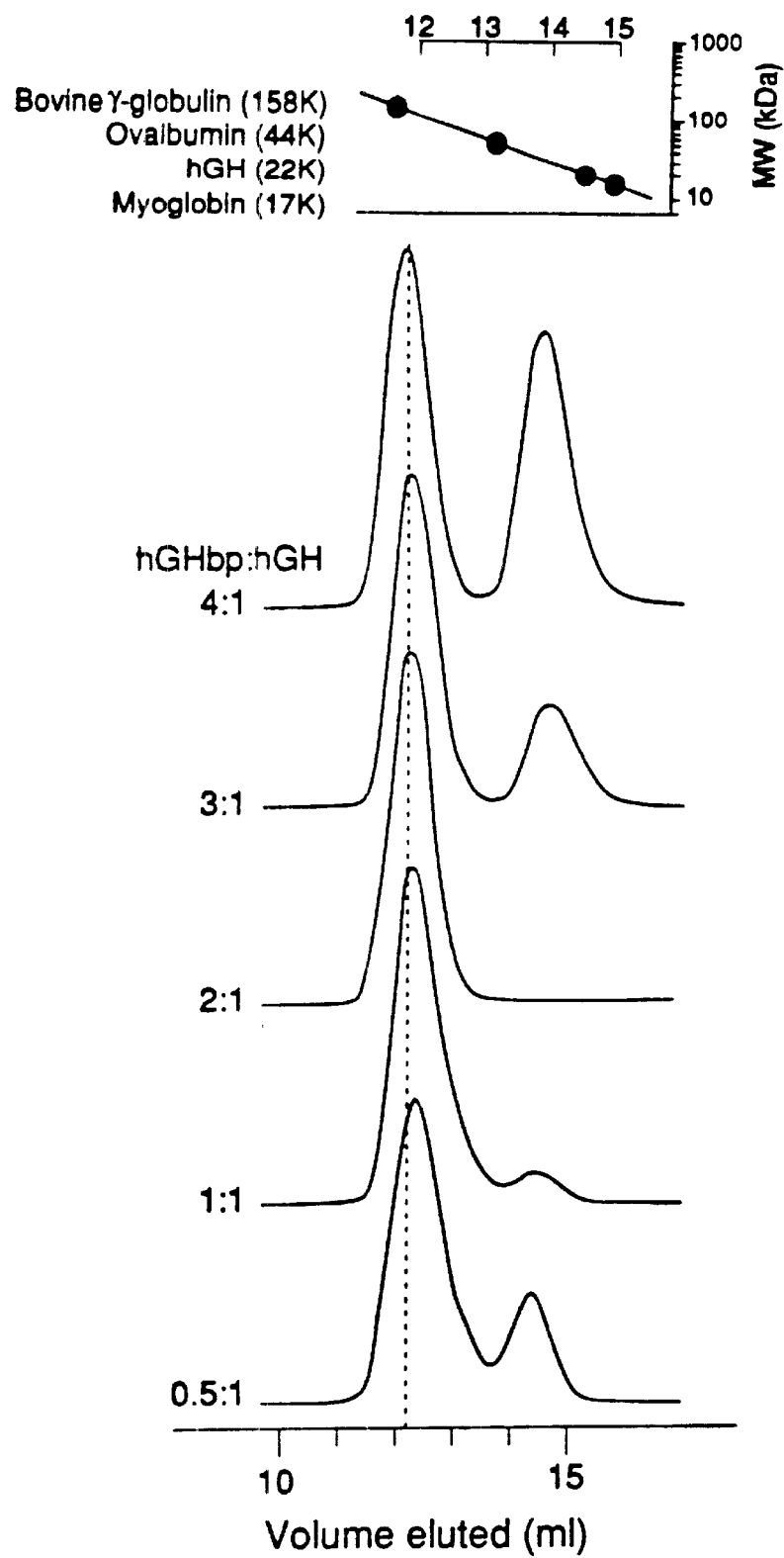
FIG. 2. Gel filtration chromatography of various ratios of hGHbp and hGH corresponding to 4:1, 3:1, 2:1, 1:1, 0.5:1. The concentrations of hGH (fixed at 10 μM except at 1:1 and 0.5:1 ratios where hGH was 20 μM and 40 μM, respectively) and hGHbp in each mixture were based upon absorbance at 280 nm. One hundred microliter protein samples were applied to a sepharose 12 FPLC column (Pharmacia) and eluted. Peaks were monitored for absorbance at 280 nm.

The extracellular domain of the EGF receptor (EGFbp) has been crystallized in complex with one molecule of EGF (Gunther, N., et al., *J. Biol. Chem.* 265:22082–22085 (1990)). Binding studies and sedimentation analysis indicate the formation of a 1:1 EGF.EGFbp complex in solution. These data suggested that the extracellular domain is insufficient to undergo hormone induced dimerization. However, it is noteworthy that the binding studies used anti-EGF receptor polyclonal antibodies to precipitate the complex. Furthermore, the crystallization and sedimentation experiments used a large excess of hormone over receptor. In our case, Mabs raised against the natural GH receptor block dimerization (FIG. 3) and a large excess hGH will dissociate the hGH.(hGHbp)$_2$ complex into a monomeric complex (FIG. 2, Ref. 34).

This later effect may have important pharmacologic implications. hGH is naturally produced in pulses that exceed 5 nM in serum and levels drop quickly to well below 1 nM (Taylor, A. L., et al., *J. Clin. Invest.* 48:2349 (1969); Thompson, R. G., et al.,*J. Clin. Invest.* 51:3193 (1972); Ho, K. Y., et al., *J. Clin. Endocrinol. Metab.* 64:51–58 (1987)). However, the hGHbp is present naturally in serum at a constant level of about 0.5 to 1 nM (Baumann, G., et al., *J. Clin. Endocrinol. Metab.* 62:134–141 (1986); Herington, A. C., et al., *J. Clin. Invest.* 77:1817–1823 (1986)). Thus, as hGH is pulsed in excess over the hGHbp one would expect it to produce 1:1 complexes with the hGHbp as well as free hGH that could interact with cellular receptors (even producing heterodimeric complexes having the form hGH.hGHbp.hGH membrane-receptor).

We have determined that hGH interacts with hGHbp to make a complex of the form hGH(hGHbp)$_2$ and have proposed that the resulting dimerization of the extracellular receptor domain initiates somatogenic signal transduction for this hormone. Since the recruited hPL and hPRL analogs (Example 4) do not promote hGHbp dimerization we can conclude that the hPL and hPRL scaffolds lack necessary dimerization determinants which are distinct from those required for receptor recognition and binding. To localize the domains involved, a series of hGH mutants with hPL or hPRL homolog substitutions, and two deletion analogs, were screened for reductions in hormone induced receptor dimerization. Important side chains were then identified by a more detailed alanine-scanning strategy.

Figure 8:
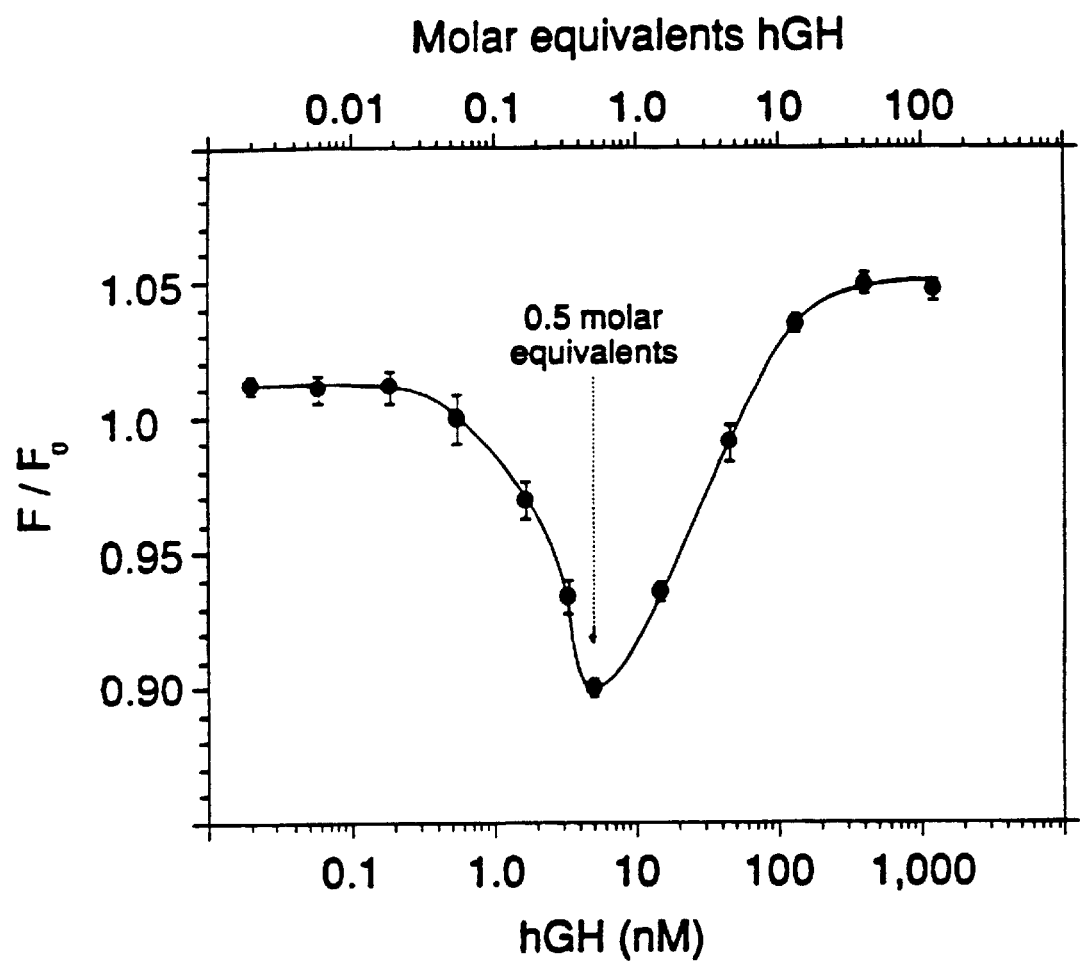
FIG. 8. Homoquenching of 10 nM S237C-AF by serial addition of hGH. After incubation, fluorescence measurements were made at an excitation λ of 490 nm and an emission λ of 512 nm (bandwidths are 3 nm and 10 nm, respectively) using a Shimadzu RF5000U Spectrofluorophotometer.

A hGHbp variant (S237C) was constructed and fluorescently labeled. Fluorescence quenching was measured to monitor hormone induced dimerization as shown in FIG. 8. This quenching indicated a 1:2 molar ratio of hGH to hGHbp (Example 4). A series of homolog-scan hGH variants with hPL and hPRL segment substitutions were tested in the fluorescence assay (Table 2). Four of these caused significant reductions in hormone induced hGHbp dimerization (Example 4). In the other two hGH deletion analogs, the loss in hGHbp dimerization appears to be due to disruptions in secondary site hGHbp binding (Table 2).

The mutant hGHbp (S237C-AF) was fluorescently labeled. This fluorescent signal was used to monitor hormone induced dimerization as shown in FIG. 8. The hGH is serially diluted against a fixed 10 nM concentration of S237C-AF and fluorescence quenching measured at equilibrium. Homoquenching of the fluorescein label increases with hGH addition and becomes maximal at 0.5 molar equivalents of hGH. However, quite strikingly, this homoquenching is reversed at higher concentrations of hGH indicating hGH.(hGHbp)$_2$ dissociates to hGH.hGHbp monomeric complex in the presence of excess hGH.

A series of homolog-scan hGH mutants with hPL and hPRL segment substitutions were tested in the S237C-AF based assay (table 2). Three of these, hPRL(12–19), hPRL (54–74) and hPRL(111–109) caused significant reductions (18, 6 and >100 fold). Losses in primary site (site 1) binding for these mutants appear to largely account for the observed reductions in hGHbp dimerization. Furthermore, mutations of primary site determinants (eg R64A and K172A/F176A) which reduce binding affinity have also been shown to reduce dimerization and an hGH mutant (E174A) shown to enhance hGHbp affinity for the primary site also enhances dimerization as measured in our assay. In addition to the homolog-scan mutants, an hGH deletion analog (deletion 1–8) showed a dramatic reduction (>100 fold) in ability to induce hGHbp dimerization (Example 4). This loss in hGHbp dimerization also appeared to be due to disruptions in secondary site hGHbp binding.

Specific amino acid specific side chains involved in secondary site hGHbp binding were probed by alanine scanning (Example 6). An analysis of 26 alanine mutants (table 3) revealed only two mutants, F1A and I4A which cause >10-fold disruptions in hGHbp dimerization and 4 others (L6A, R8A, D116A, E119A) carrying >2-fold disruption. These determinants are different from those crucial for primary site binding; Experiments in which sequential hGH additions are made to a fixed concentration of S237C-AF (100 nM), and fluorescence homoquenching showed rapid equilibration times (<3 minutes) for hGH induced dimerization and slow equilibration times (>30 minutes) for subsequent reversal of dimerization by excess hGH. This suggests that reversal of dimerization is off-rate limited (Example 6 for mechanism).

The formation of hGH(hGHbp)$_2$ crystals permits the determination of the three-dimensional structure of the hGH (hGHbp)$_2$ complex using x-ray chrstallographic techniques following the methods described in Blundell and Johnson, Academic Press, London, 1976. This structure is illustrated in FIG. 11 and discussed in Example 7 below. The structure of FIG. 11 indicates that each hGH is bound to two hGH receptors, or hGHbp. Each hGHbp is in contact with different portions of the hGH; the hGH amino acids in contact with the first hGHbp are shown in Table 4; and, the hGH amino acids in contact with the second hGHbp are shown in Table 5. The contacting amino acids between the two hGHbp are shown in FIG. 6.

Variants of hGH can be made at these amino acid contact points and detected by the assay method of the present invention. hGHbp variants similarily can be made in those amino acids involved in the binding to the hGH or between the two hGHbp themselves. Such hGHbp variants can detected using the assay methods of the present invention using wild type hGH and hGHbp.

Therapeutic Compositions and Administration of Ligand Analogs and GHBP Antibodies Therapeutic formulations of ligand analogues or GHbp antibody are prepared for storage by mixing the ligand analogues protein having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides (to prevent methoxide formation); proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

Ligand analogues or GHGp antibody to be used for in vivo administration must be sterile. This is readily accomplished by filtration through sterile filtration membranes, prior to or following lyophilization and reconstitution. Ligand analogues or antibody to a ligand analogues ordinarily will be stored in lyophilized form or in solution.

Therapeutic ligand analogues, or ligand analogues specific antibody compositions generally are placed into a container having a sterile access port, for example, an intravenous solution bag or vial having a stopper pierceable by a hypodermic injection needle.

The route of administration of ligand analogues or GHbp antibody is in accord with known methods, e.g., injection or infusion by intravenous, intraperitoneal, intracerebral, intramuscular, intraocular, intraarterial, or intralesional routes, or by sustained release systems as noted below. Ligand analogues are administered continuously by infusion or by bolus injection. GHbp antibody is administered in the same fashion, or by administration into the blood stream or lymph.

Suitable examples of sustained-release preparations include semipermeable matrices of solid hydrophobic polymers containing the protein, which matrices are in the form of shaped articles, e.g. films, or microcapsules. Examples of sustained-release matrices include polyesters, hydrogels [e.g., poly(2-hydroxyethyl-methacrylate) as described by Langer, et al., *J. Biomed. Mater. Res.*, 15:167–277 (1981) and Langer, *Chem. Tech.*, 12:98–105 (1982) or poly (vinylalcohol)], polylactides (U.S. Pat. No. 3,773,919, EP 58,481), copolymers of L-glutamic acid and gamma ethyl-L-glutamate (Sidman, et al., *Biopolymers*, 22:547–556 [1983]), non-degradable ethylene-vinyl acetate (Langer, et al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133, 988). While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release ligand analogues or antibody compositions also include liposomally entrapped ligand analogues or antibody. Liposomes containing ligand analogues or antibody are prepared by methods known per se: DE 3,218,121; Epstein, et al., *Proc. Natl. Acad. Sci. USA*, 82:3688–3692 (1985); Hwang, et al., *Proc. Natl. Acad. Sci. USA*, 77:4030–4034 (1980); EP 52,322; EP 36,676; EP 88,046; EP 143,949; EP 142,641; Japanese patent application 83-118008; U.S. Pat. No. 4,485,045 and U.S. Pat. No.

4,544,545; and EP 102,324. Ordinarily the liposomes are of the small (about 200–800 Angstroms) unilamelar type in which the lipid content is greater than about 30 mol. % cholesterol, the selected proportion being adjusted for the optimal ligand analogues therapy. Liposomes with enhanced circulation time are disclosed in U.S. Pat. No. 5,013,556.

Use of Variants

Antagonist ligand variants selected by the assay of the present invention are used in therapeutic formulations or expressed in transgenic animals to act as antagonists, blocking the action of the naturally occuring ligand. Transgenic animals are useful as novelties or as experimental models. Other selected ligand variants are used in therapeutic formulations to act as agonists, administered to potentiate or to promote a response similar to that stimulated by the naturally occuring cytokine. For example, hGH variants are used in a pharmaceutically effective dosage formulation (e.g., U.S. Pat. No. 5,096,885 filed Apr. 15, 1988). Ligand variants are advantageous in that they may have an activity similar to the naturally occuring cytokine, but with reduced or eliminated undesirable side effects, one such example being an hGH variant that does not exhibit diabetogenic activity. Ligand variants which have no biological activity, either as agonists or antagonists, are useful in immunoassays for the wild type ligands or their antibodies since they will retain at least one ligand immune epitope.

Monoclonal Antibody and Stimulation of Receptors

We have determined that certain antibodies are capable of stimulating the hGH receptor, i.e., they are capable of crosslinking the receptors in a fashion that mimics the ability of hGH to form a ternary complex and activate the receptor. Examples of such agonist antibodies were already known at the time of this invention, but their ability to act as agonists of hGH was unappreciated. Suitable antibodies are MAb 263 (Barnard, et al., *Endocrinology*, 115:1805–1813 [1984] or Barnard, et al., *Biochem. J.*, 231:459–468 [1985]). Others are MAbs 13E1 and 3D9, produced by methods described below. These antibodies optionally are used to create chimeras or CDR grafted forms that are less immunogenic than the parental antibodies in the intended host. The antibodies preferably are directed against the human receptor. Agonists for hGH must be at least bivalent. However, monovalent antibodies such as FAb fragments, which only bind to one receptor molecule, are useful as antagonists.

The bivalent antibodies are bispecific in some embodiments. Thus, one arm of the antibody is directed against one receptor epitope while the other arm is directed against another epitope on the receptor. Antagonist antibody embodiments can contain one arm directed to the receptor (preferably its receptor-receptor contact region) with another arm directed at an antigen other than GH receptor. The antibodies are made by conventional hybridoma methods or by conventional hydridoma methods or by recombinant methods wherein the recombinant cell is transformed with heavy and light chain encoding each arm. Bispecific antibodies are made by recombinant methods and recovered by affinity purification from the cell culture, or the antibodies are made separately and recombined in vitro by conventional methods.

These results are of particular interest in the veterinary field since it is now possible to raise such antibodies in vivo by immunizing the animals against the growth hormone receptor or fragment thereof so as to generate GH agonists by active immunization. Thus, antibodies are administered either passively (by administration of exogenous antibody) or actively by immunization with receptor.

The agonist antibodies are administered in dosages based on their affinity in comparison to growth hormones. Further dosages for mammals are readily extrapolated from the rat growth study described infra. Antagonist antibodies are administered in dosages calculated to complete with sufficient growth hormone to reduce the effective activity thereof to normal ranges or to below normal if dwarf animals are the objective.

The antibodies are formulated and administered in substantially the same fashion as the ligand analogues as described above. The agonist antibodies are used for the same purposes as growth hormone has been used heretofore.

The following examples are intended to illustrate the best mode now known for practicing the invention, but the invention is not to be considered limited to these examples.

EXAMPLE 1

Structure of the hGH-Receptor Complex

The assay methods of the present invention are based upon the discovery of the hGH-receptor complex structure; that is, one hGH and two hGH receptors or binding proteins forming a stable complex that may be detected. These assay methods are exemplified by the hGH(hGHbp)$_2$ complex assay methods.

Crystallization of the hGH.(hGHbph Complex

Figure 1A:
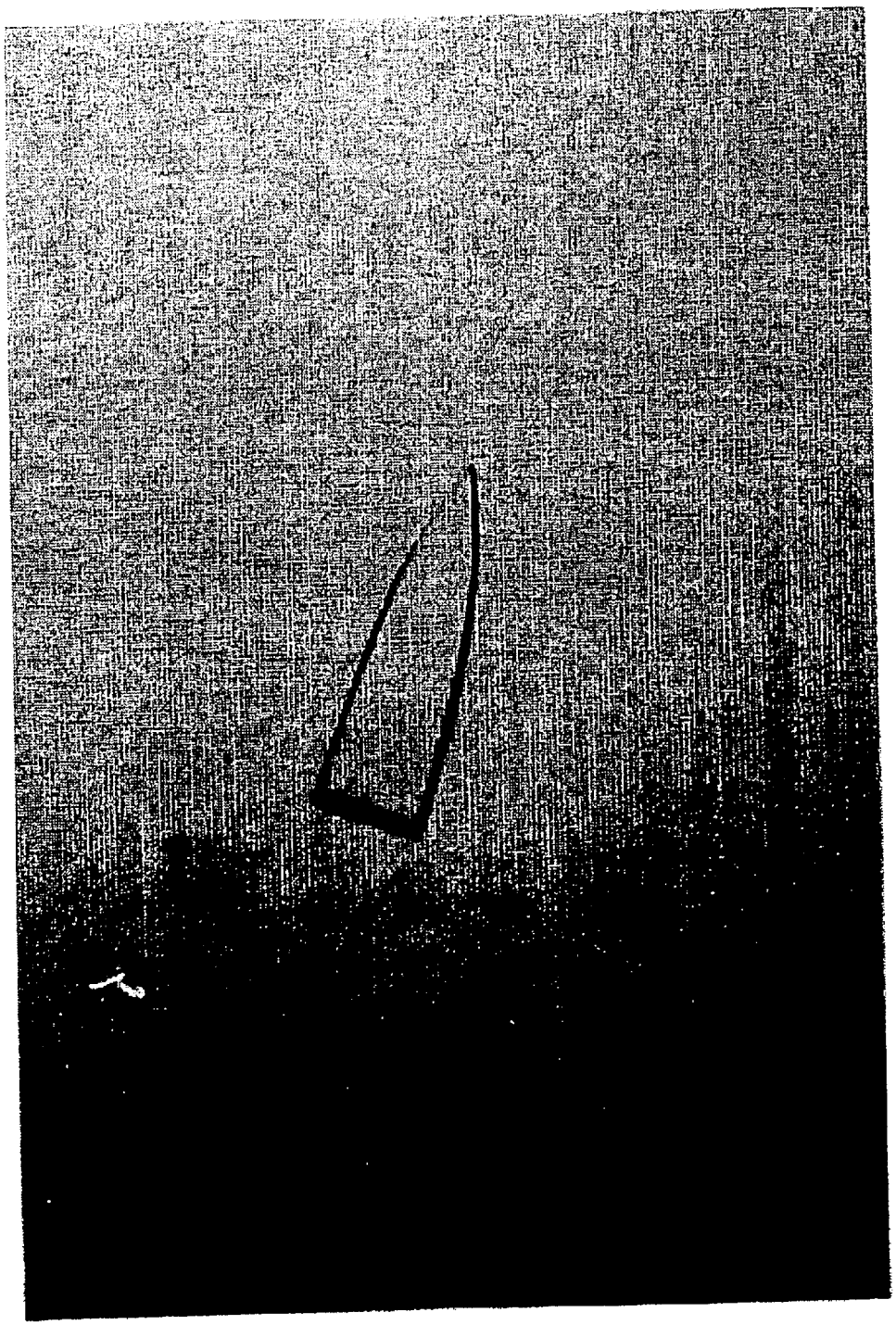
FIGS. 1a and 1b.

Crystals of the complex between hGH (22 kDa) and the hGHbp (28 kDa) (FIG. 1a) were grown by vapor phase diffusion (A. McPherson, in Preparation and Analysis of Protein Crystals, John Wiley and Sons, New York, (1982)). The crystals diffract to at least 2.7 Å and belong to space group (P2$_1$ 2$_1$ 2) with unit cell parameters of a=145.8 Å, b=68.6 Å, c=76.0 Å. The volume of the asymmetric unit of these crystals is such that the complex is unlikely to have the form of either hGH.hGHbp or (hGH.hGHbp)$_2$. In particular, the solvent content would have to be too high (68%) for a 1:1 complex, or too low (32%) for a 2:2 complex in the unit cell. Since the typical solvent content of crystals is about 50% (Matthews, B. W. *J. Mol. Biol.* 33, 491–497 (1968)) it was most likely that these crystals contain an asymmetric mixture of the components.

Figure 1B:
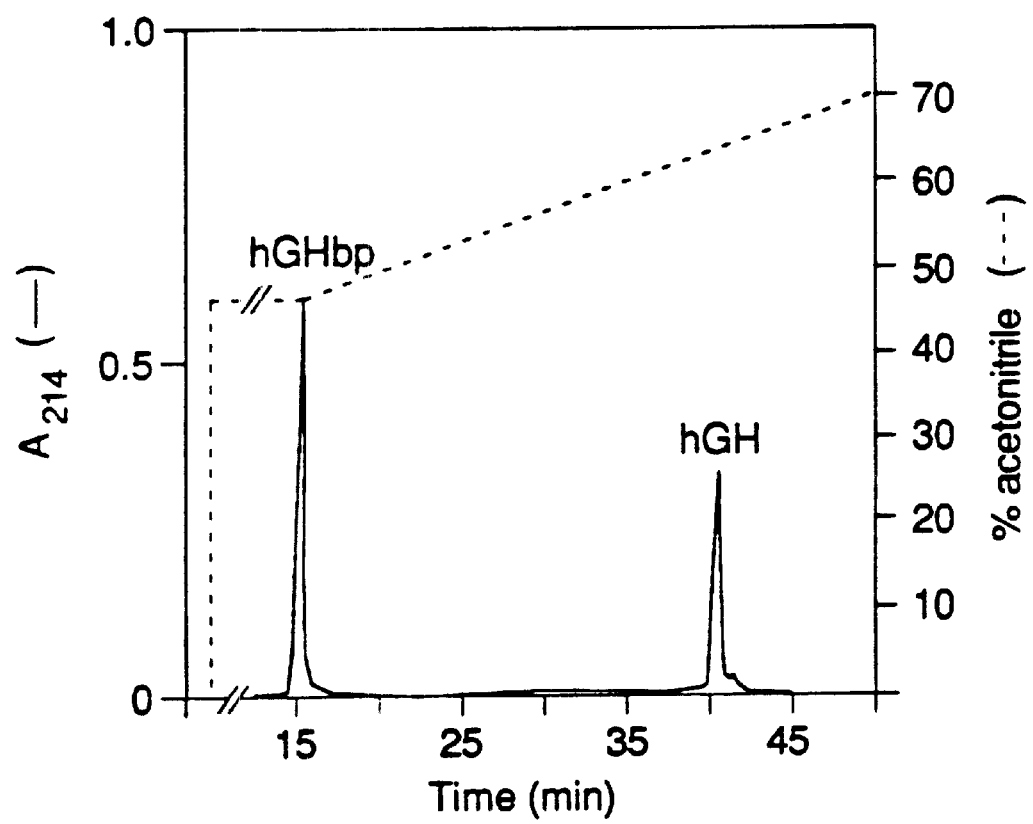

To evaluate the precise composition of the crystals they were dissociated in 0.1% trifluoroacetic acid and chromatographed under denaturing conditions (FIG. 1b). The amount of hGH and hGHbp was quantified by integration of their respective peaks that were monitored at 214 nm, which corresponds to the absorbance of peptide bonds. From four independent determinations, the ratio of the A$_{214}$ of the hGH peak to the hGHbp peak was 0.42±0.02. For a complex having the form hGH.(hGHbp)$_2$, the ratio predicted for integrated peak areas is 0.40 based upon the number of residues in each of the components (191 residues for hGH and 238 residues for the hGHbp). In control experiments, a 1:2 mixture of hGH to the hGHbp produced essentially the same chromatogram as FIG. 1B whereas 2:1 and 1:1 mixtures generated expected and different chromatograms. Therefore, the crystals in FIG. 1 contained hGH and hGHbp in a 1:2 molar ratio. The ability of hGH and hGHbp to form a stable complex in solution confirms that complex formation is a reliable assay parameter.

Formation of the hGH (hGHbp)$_2$ Complex in Solution

The existance of the hGH (hGHbp)$_2$ complex was established in solution by size exclusion chromatography. hGH and the hGHbp were mixed in ratios of 1:4, 1:3, 1:2, 1:1 and 1:0.5 and the components were separated by gel filtration on a Superose 12 FPLC column (FIG. 2). At a 1:4 ratio of hGH to hGHbp two peaks are present of apparent molecular weight 70 kD and 30 kD corresponding to a hGH.(hGHbp)$_2$ complex and free hGHbp, respectively. The areas of the peaks are dominated by the absorbance of the hGHbp because its $\in_{280}{}^{0.1\%}$ is 2.9-fold higher than hGH 12. The $\in_{280}{}^{0.1\%}$ for hGH is 0.82 cm$^{-1}$ and 2.35 cm$^{-1}$ for the hGHbp based on absorbance and compositional analysis of a pure sample. At 1:3 and 1:2 ratios of hGH to hGHbp there is no change in the shape or position of the complex peak; however the peak corresponding to the free hGHbp is progressively reduced to zero. Thus at a 1:2 ratio, virtually all of the hGH and hGHbp are bound in a complex. As the ratio of hGH to hGHbp is adjusted to 1:1 and finally 1:0.5, the position of the complex peak shifts to a smaller size (~55 kD), becomes asymmetric, and free hGH accumulates, thereby suggesting there is a mixture of species corresponding to hGH.(hGHbp)$_2$, hGH.hGHbp and monomeric hGH. SDS-PAGE of protein samples taken across these peaks confirmed the assigned compositions. Additional control experiments showed that the free components run as monomeric proteins indicating that dimerization requires the presence of both hGH and the hGHbp under these conditions. Therefore, complex formation is detectable by multiple assay methods and hGH.(hGHbp)$_2$ complex formation serves as an indicator of hGH binding to cellular receptors. Similarly, any cytokine acting through a cytokine receptor which forms a cytokine-cytokine receptor complex, analogous to the hGH-hGH receptor complex, can be evaluated by such assay procedures.

EXAMPLE 2 hGH Receptor Binding Sites

The nature of hGH binding sites for hGH receptor or hGH binding protein was characterized using antibody that blocked hGH binding sites for the receptor or binding protein. The evidence for two binding sites on the hGHbp is as follows.

The affinity of hGH for the hGHbp is typically measured by displacement of [$^{125}$I]hGH from the hGHbp and precipitating the complex with an anti-receptor monoclonal antibody (Mab5) produced from glycosylated rabbit GH receptor (Barnard, R. et al., *Endocrinology* 115:1805–1813 (1984); Barnard, R. et al., *Biochem. J.* 231:459–468 (1985)). Using this assay, Scatchard analysis demonstrated that hGH and the hGHbp were capable of forming a 1:1 complex (Leung D. W. et al., *Nature* 330:537 (1987); Fuh G., et al., *J. Biol Chem.* 265:3111–3115 (1990); Barnard, R., et al., *Endocrinology* 115, 1805–1813 (1984); Barnard, R., et al., *Biochem. J.* 231:459–468 (1985); Spencer, S. A., et al., *J. Biol Chem.* 263:7862–7867 (1988).Spencer, S. A., et al., *J. Biol Chem.* 263:7862–7867 (1988)).

Recently, additional Mabs have been produced by immunization with the unglycosylated hGHbp purified from *E. coli* (Fuh G., et al., *J. Biol. Chem.* 265:3111–3115 (1990)). Scatchard analysis of displacement curves (FIG. 5) using two of these anti-hGHbp Mabs (3B7 and 3D9) to precipitate the complex give higher binding affinities (K$_D$ 0.1 nM versus 0.4 nM for Mab5) and stoichiometries of 0.5 hGH to 1 hGHbp. These results can be explained if Mab5 were to block determinants on the hGHbp for binding to a second site on hGH. The lack of cooperativity in assays using Mab3B7 and 3D9 is likely to reflect the fact that the affinity of hGH in the 1:1 complex (as measured using Mab5) is only about four-fold weaker than for the 1:2 complex (as measured using Mab 3B7 and 3D9). A much greater differential affinity would be needed to pick up positive cooperativity by upward inflections on a Scatchard plot. Moreover, Mab 3B7 and 3D9 should precipitate both 1:1 and 1:2 complexes which would dampen any apparent cooperativity. Therefore, blockage of the hGH second binding site results in a 1:1 hGH.hGHbp molar ratio; while antibody that does not block the second binding site results in a 1:2 molar ratio.

The evidence for two binding sites on hGH is the following. Mab5 was employed in the scanning-mutational analysis of binding determinants between hGH and the hGHbp. Therefore, the determinants identified in these studies reflect those important for modulating formation of the 1:1 complex. Based upon this data we have installed these determinants into non-binding homologs of hGH and created analogs that bind tightly to the hGHbp (Cunningham, B. C., et al.,*Science* 247:1461–1465 (1990)). For example, wild-type human prolactin (hPRL) or human placental lactogen (hPL) bind to over 10$^5$ or 10$^3$-fold more weakly to the hGHbp than does hGH, respectively. By incorporating 8 substitutions into hPRL. (E62S/D63N/Q66E/H171 D/E174A/N175T/Y176F/K178R; (Cunningham, B. C., et al., *Science* 247:1461–1465 (1990)) or 5 into hPL (V4I/D56E/M64K/E174A/M179I); we have produced variants that bind to the hGHbp only 62- or 1.4-fold weaker than hGH, respectively.

Figure 3:
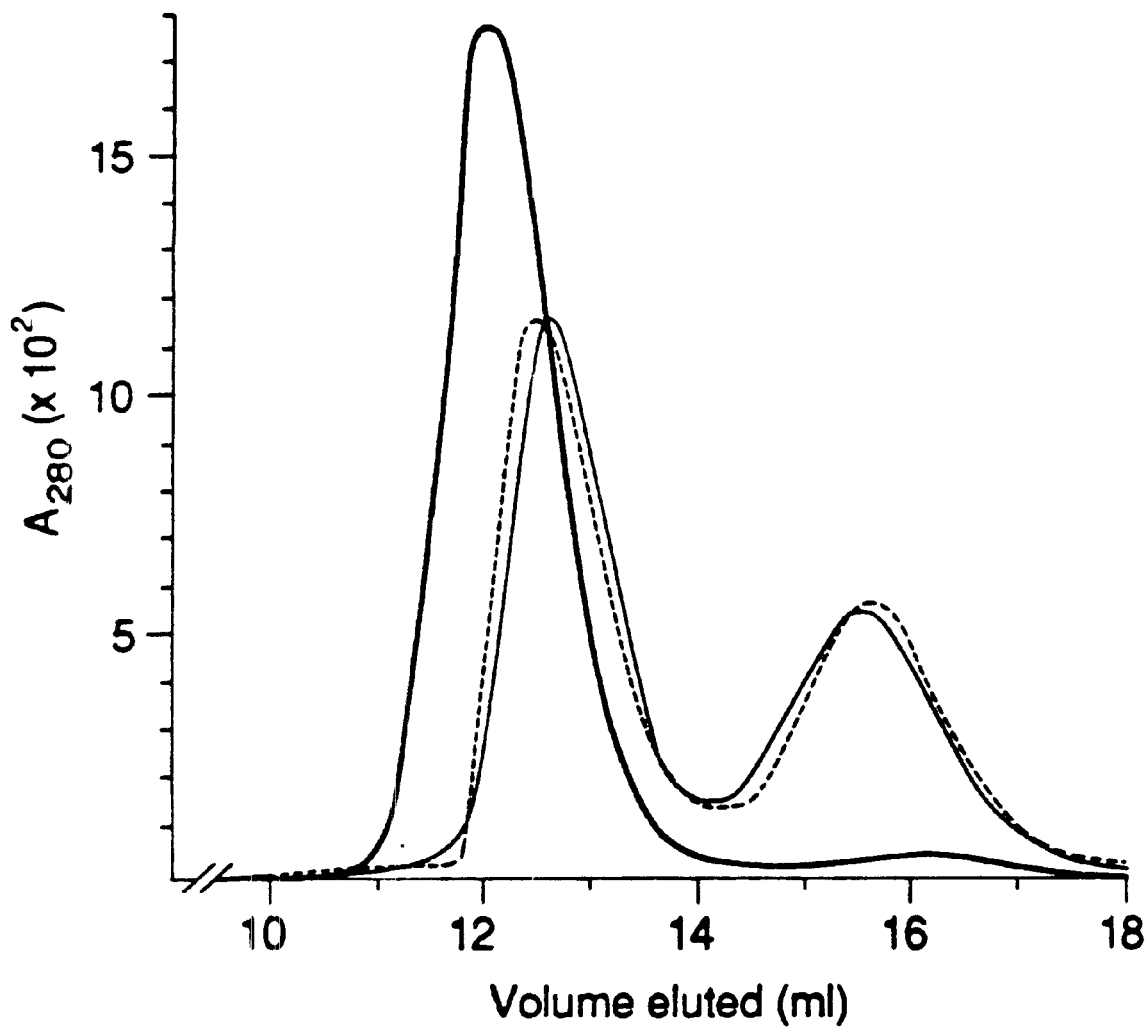
FIG. 3. Gel filtration chromatography of a 2:1 ratio of hGHbp:hGH (bold, solid line) and variants of human prolactin or human placental lactogen (other lines) that were engineered to bind to the hGHbp.
Figure 4:
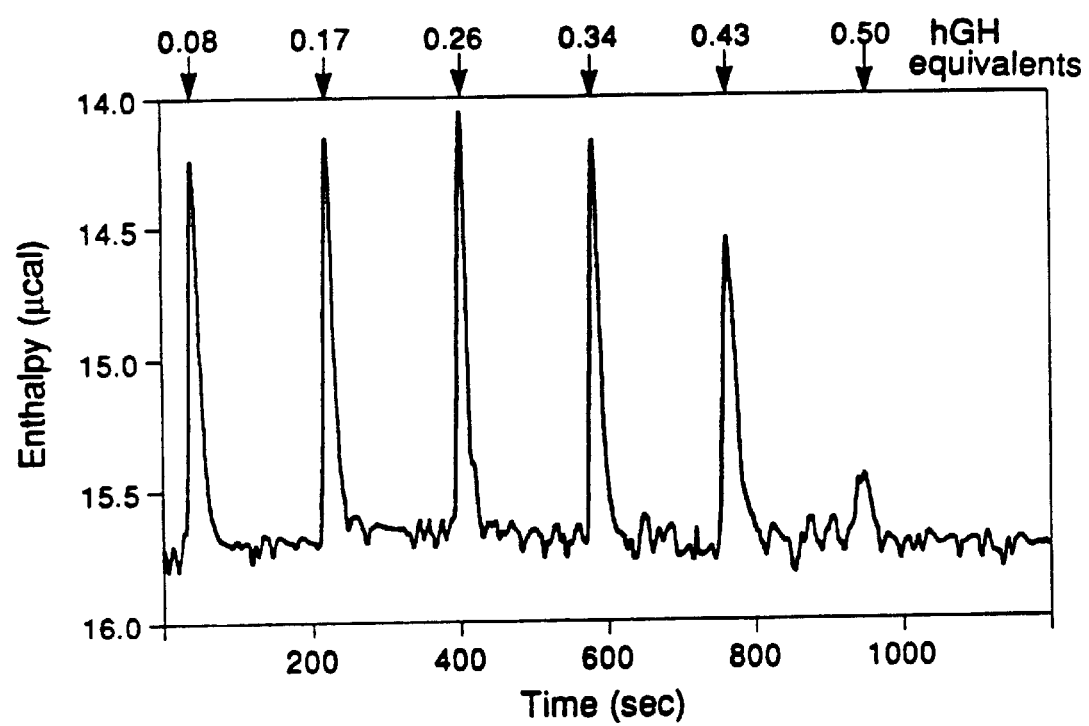
FIG. 4. Titration calorimetry of hGH with hGHbp. The hGHbp (at 15 μM in 10 mM Tris (pH 8.0)) was placed in a 1.37 ml titration cell (MC2 ml titration calorimeter, Microcal Incorporated, Northampton, Mass.) and equilibrated at 25° C. To this solution, hGH (437 μM in 10 mM Tris (pH 8.0) was added in 4 μL increments. Each injection occurred over 8 seconds with an interval of 5 minutes between each injection.

We used gel filtration to determine if these variants could bind to one or two molecules of the hGHbp (FIG. 3). At a 2:1 ratio of hGHbp to hormone, both binding variants of hPRL and hPL show two symmetrical peaks corresponding to a 1:1 complex with the hGHbp (apparent molecular weight of about 55 kDa) and a lower molecular weight peak (30 kDa) representing a stoichiometric excess of the hGHbp. Under identical conditions, the wild-type hGH produces a single peak (apparent molecular weight 77 kDa) corresponding to the hGH.(hGHbp)$_2$ complex. The small satellite peak is from a slight excess of hGHbp. Peak compositions were confirmed by SDS-polyacrylamide gel electrophoresis (SDS-PAGE).

We employed scanning calorimetry to further evaluate the stoichiometry and heat of reaction because binding can be studied free in solution without the need to employ antibodies or chromatography to separate complexes. To a solution containing a fixed concentration of the hGHbp (15 μM), aliquots of hGH were added and the heat of reaction was measured until there was no further enthalpic change (FIG. 5). This experiment allowed us to determine the equivalents of hGH bound to the hGHbp and the heat of reaction.

In Table 1d we summarize the titration end points and heats of reaction for wild-type hGH and variants of hGH and hPRL. The ratio of hGH necessary to bind to all of the hGHbp is about 0.5 to 1. Furthermore, a series of single alanine mutants that reduce binding (by up to 20-fold) or enhance binding (by 4.5-fold) give the same stoichiometry of binding as wild-type hGH to the hGHbp albeit with changes in the enthalpy of the reaction. In contrast, the stoichiometry of binding of the hPRL variant to the hGHbp is 0.85 to 1.

TABLE 1d

Stoichiometries and heats of reaction with the hGHbp for wild-type and alanine mutants of hGH and a variant of hPRL that binds tightly to the hGHbp.

| Protein | $K_D$ (nM)[a] | mol hGH/mol GHbp at the end point[b] |
|---|---|---|
| wt hGH | 0.34 | 0.46 ± 0.05 |
| R64A | 7.1 | 0.47 ± 0.07 |
| K172A | 4.6 | 0.48 ± 0.1 |
| I58A | 5.6 | 0.48 |
| F176A | 5.4 | 0.46 |
| E174A | 0.08 | 0.47 |
| hPRL variant | 2.1 | 0.85 |

[a]Values taken from Cunningham B. C., et al., Science 244: 1081 (1989) for formation of a 1:1 hGHhGHbp complex using the Mab5 immunoprecipitation assay. Calorimetry is not suitable for measuring binding constants for the dimeric complex in the nanomolar range because the calorimeter is not sensitive to enough to accurately determine the change in the heat of reaction for components whose concentrations would need to be set below the binding constant.
[b]Average (±SE) of duplicates; others were single determinations.

Altogether these data strongly indicate that the hPRL and hPL variants were missing important determinants for dimerization of the hGHbp. These determinants are largely conserved in the single alanine mutants of hGH but not in the hPRL or hPL variants. This suggests there are two binding sites on hGH for the hGHbp. One of these sites has been functionally characterized in detail by alanine-scanning mutagenesis of hGH (Cunningham B. C., et al., Science 244:1081 (1989)) or hGHbp using the Mab5 immunoprecipitation assay, respectively. The second sites on hGH and the hGHbp remained to be elucidated and are described infra.

EXAMPLE 3 hGH-Receptor Complex and Spectral Change

Binding of hGH to its receptor causes little spectral change in the components. To determine if the binding of hGH to the hGHbp causes large changes in secondary or tertiary structure of the components we investigated the change in the circular dichroic (CD) and fluorescence spectra upon complex formation Proteins were prepared for spectroscopy by dialyzing approximately 1.0 mg/ml protein in 0.01 M Tris pH (8.0) and 200 mM NaCl. After dialysis the solutions are filtered (0.22µ, Millipore) and the absorbance spectrum was obtained. The spectra were corrected for light scattering (Shauenstein E., et al., J. Polymer Sci. 16:45 (1955)) and protein concentrations were determined by absorbance at 280 nm The $\epsilon_{280}^{0.1\%}$ for hGH is 0.82 cm$^{-1}$ and 2.35 cm$^{-1}$ for the hGHbp based on absorbance and compositional analysis of a pure sample. hGH exhibits a strongly α-helical CD spectrum (Bewley T. A., et al., Arch. Biochem. Biophys. 138:338–346 (1970)) characteristic of its 4 helix bundle structure (Abdel-Meguid S. S., et al., Proc. Natl. Acad. Sci. USA 84:6434 (1987)). In contrast, the CD spectrum of the hGHbp is characteristic of a protein composed mainly of turns and loops (Cleary, S., et al., Biochemistry 28:1884 (1989); Hilder, R. C., et al., Biophysical Chemistry 31:45 (1988)) connected by disulfide bonds; the hGHbp contains 3 adjacently linked disulfide bonds (Fuh G., et al., J. Biol. Chem. 265:3111–3115 (1990)). Frozen cell paste was thawed in hypotonic buffer (10 mM Tris pH 8.0, 1 mM PMSF (Sigma), 2 mM EDTA). The suspension was homogenized, stirred for 1 hr at 4° C., and then centrifuged at 10,000×g for 20 min. To the supernatant was added solid ammonium sulfate at 260 g/L and stirred until dissolved. The protein precipitate was collected by centrifugation at 10,000×g for 30 min. The pellet was resuspended in 10 mM Tris pH 8.0, 1 mM PMSF, and dialyzed against the same buffer. The dialysate was applied to a Q Sepharose column (Pharmacia) in 10 mM Tris (pH 8.0) and eluted with a linear gradient of 0.0 to 0.5 M NaCl. Peak fractions containing the hGHbp were loaded directly onto an hGH affinity column. After washing, the column was eluted with 4 M MgCl$_2$, 10 mM Tris pH 7.5. The peak fractions were combined and dialyzed with 10 mM Tris pH 7.5, applied to a Mono Q column, washed and eluted in 10 mM Tris pH 7.5 with a linear gradient of 0.0 to 0.2 M NaCl.

When hGH and the hGHbp are mixed the far UV CD spectrum is virtually identical to the sum of the spectra for hGH and hGHbp (FIG. 6A). This result indicates the absence of large changes in regular secondary structure upon complexation. The near UV CD spectrum (FIG. 6B) reflects the asymmetric environment of the aromatic amino acid side chains (Bewley, T. A. Recent Progress in Hormone Research 35:1555 (1979); Bewley T. A., et al., Archives of Biochemistry and Biophysics 233:219–227 (1984)). There are large differences between the UV absorbance spectra of hGH and the hGHbp, largely a result of the greater tryptophan content of the hGHbp compared to hGH (9 versus 1, respectively). However, except for an increase in the intensity of the spectrum the sum of the individual spectra are essentially identical to that obtained after mixing.

In the fluorescence spectrum, there is a blue shift from 340 nanometers to 334 nanometers and slight reduction in the fluorescence intensity upon hGH binding to the hGHbp (FIG. 7). Iodide quenching and Stem-Volmer analysis indicate there is a reduction in the exposure of tryptophan in the hormone receptor complex. This is likely the result of burying one or more Trp residues in the hGHbp upon binding hGH because fluorescence quenching studies have shown that the tryptophan in hGH is not appreciably exposed to solvent (Bewley, T. A., Recent Progress in Hormone Research 35:1555 (1979); Bewley T. A., et al., Archives of Biochemistry and Biophysics 233:219–227 (1984)). In contrast, mutational analyses of the hGHbp show that Trp104 is especially important in binding to hGH. While these spectral studies show little conformational change upon binding of hGH to the hGHbp, these methods are biased to structural changes in regular secondary structure (far UV CD) and changes in positions of aromatic groups (near UV CD and fluorescence quenching). Therefore, a high resolution structure of the complexed and free components may still reveal conformational changes.

EXAMPLE 4

Assay Method and Modified hGH

Modified polypeptide hormones were evaluated in the assay method. A set of hGH residues (including F10, F54, E56, I58, R64, Q68, D171, K172, E174, F176, R178 and V185) are known to be important for confering high affinity stoichiometric binding to hGHbp (WO 90/04788). These determinants were installed in the hGHbp-binding-incompetent hGH homologs, human placental lactogen (hPL) and human prolactin (hPRL) so as to identify hPL and hPRL analogs that bind hGHbp tightly (Kd=1 nM and 6 nM, respectively). As previously discussed, hGH interacts with hGHbp to make a complex of the form hGH(hGHbp)$_2$. Since the recruited hPL and hPRL analogs do not promote hGHbp dimerization we can conclude that the hPL and hPRL scaffolds lack necessary dimerization determinants which are distinct from those required for initial receptor recognition and binding. To localize the domains involved in forming hGH(hGHbp)$_2$, a series of hGH mutants with hPL or hPRL homolog substitutions, and two deletion analogs, were screened for reductions in hormone induced receptor dimerization. Important side chains were then identified by a more detailed alanine-scanning strategy.

To quantitate hormone induced hGHbp dimerization we utilized a sensitive assay measuring homoquenching of fluorescein-labeled hGHbp. A mutant hGHbp, S237C, was constructed, purified and reacted with 5-iodoacetamidofluorescein (5-IAF) to yield fluorescently labeled hGHbp (S237C-AF). The resulting S237C-AF reagent possesses one label per hGHbp molecule and retains full binding activity in a competitive binding assay. Since fluorescein has excitation and emission spectra which overlap, this fluorescent probe undergoes homoquenching as these molecules approach one another. This signal was used to monitor hormone induced dimerization of S237C-AF as shown in FIG. 8.

In FIG. 8, homoquenching of 10 nM S237C-AF by serial addition of hGH is shown. S237C-AF was diluted to 10 nM concentration in binding buffer (20 mM tris.HCl pH 7.5, 0.1% BSA, 0,02% NaN$_3$) and 1.0 ml aliquots were dispensed to 12×75 mm polypropylene assay tubes. Separate dilutions of hGH were made over a range from 120 mM to 0.002 mM. Aliquots (10 ml of hGH dilution or buffer only were then added to S237C-AF tubes and the mixture incubated to equilibruim for 5 hours at 25° C. in the dark. After incubation, fluorescence measurements were made using an excitation I of 490 nm and an emission I of 512 nm (bandwidths are 3 nm and 10 nm, respectively) using a Shimadzu RF5000U Spectrofluorophotometer. F/Fo values were calculated from triplicate readings and plotted against hGH concentration. Preparation of S237C-AF was as follows: Mutant S237C hGHbp was constructed and purified as previously described. A solution of 1 mg/ml S237C was brought to 25 mM cysteine HCl, 25 mM NaHCO$_3$ and incubated for 2 hours at 4° C. to deblock the cysteine at position 237. The protein was desalted using a PD10 (Pharmacia) mini-column equilibrated with 50 mM tris.HCl pH 8 and immeadiately reacted with 500 mM 5-IAF (Molecular Probes) for 16 hours at 4° C. in dark. DTNB analysis of deblocked S237C prior to 5-IAF addition showed an average of one free thiol group per S237C molecule (22 $\mu$M free SH vs. 17 $\mu$M S237C). The 5-IAF reacted S237C was purified from free fluorophore using another PD10 mini-column equilibrated with 20 mM tris.HCl pH 7.5. Aliquots of purified S237C-AF were stored at −80° C. and thawed just prior to use. Adsorbtion spectrum analysis of the S237C-AF shows 0.84 mM fluorescein bound per 1.0 mM S237C using molar extinction coefficients of 71,300 (at 494 nm) and 64,800 (at 280 nm) and correcting for interfering 5-IAF adsorbance at 280 nM.

Figure 9:
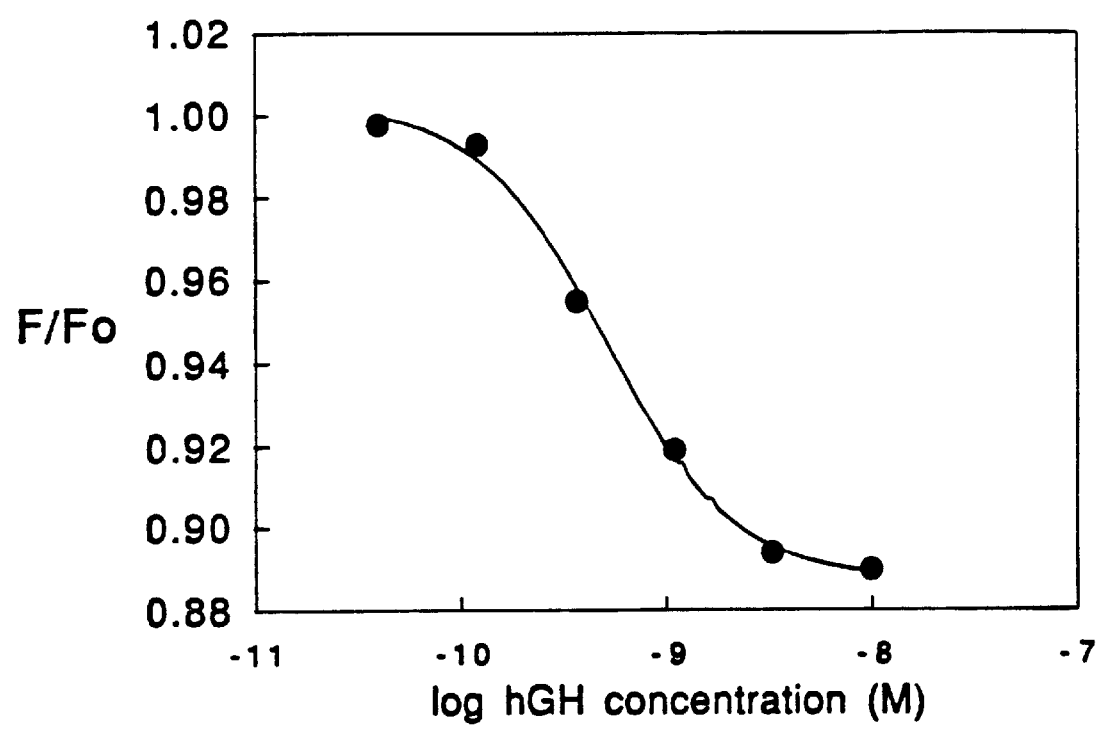
FIG. 9. $IC_{50}$ determination for hGH induced dimerization or S237C-AF. Serial dilutions (3 fold) of S237C-AF (prepared as described in FIG. 8) in binding buffer (20 mM tris.HCl pH 7.5, 0.1% BSA, 0.02% $NaN_3$) were made over a range from 20 nM to 0.08 nM and 1.0 ml aliquots were dispensed to assay tubes. Similarly, hGH was serially diluted, but over a range from 1 μM to 0.004 μM. Aliquots (10 μl) of hGH dilution (giving 1:2 molar ratio hGH to S237C-AF) and buffer only were added to the S237C-AF containing assay tubes, mixed and incubated to equilibrium for 5 hours at 25° C. in dark. After equilibration, fluorescence was measured as previously described (FIG. 8) except excitation bandwidth was 10 nM. $IC_{50}$ values are calculated as the concentration of hGH giving half-maximal Δ F/Fo values as determined from 4 parameter curve fits. An IC50 of 0.54 (+/–0.14) nM was calculated from the mean of six independent experiments.

Here, hGH was serially diluted against a fixed 10 nM concentration of S237C-AF and fluorescence quenching measured at equilibrium. Homoquenching increased with hGH addition and becames maximal ($\Delta$F/Fo=11%) at 0.5 molar equivalents of hGH (5 nM). However, quite strikingly, this homoquenching is reversed at higher concentrations of hGH indicating hGH.(hGHbp)$_2$ dissociates to hGH.hGHbp monomeric complex in the presence of excess hGH (i.e. hGH/hGHbp>0.5). The measured fluorescence homoquenching reflect genuine Forster energy transfer as shown from experiments using a nonidentical donor/acceptor pair to measure both donor (S237C-AEDANS, ref.) fluorescence quenching and acceptor (S237C-AF) fluorescence enhancement. The increase in measured fluoresence to values of F/Fo>1, that occurs in the presence of a large excess of hGH (>70 nM), appears to be due to higher non-specific binding of free S237C-AF versus bound hGH.S237C-AF complex. While this phenomenon may slightly distort IC$_{50}$ values obtained in our assay (FIG. 9), relative IC$_{50}$ values, which are the basis of our analysis, should remain unaffected In FIG. 9, the IC$_{50}$ determination for hGH induced dimerization of S237C-AF was determined. Serial dilutions (3 fold) of S237C-AF (prepared as described for FIG. 8) in binding buffer (20 mM tris.HCl pH 7.5, 0.1% BSA, 0.02% NaN$_3$) were made over a range from 60 nM to 0.08 nM and 1.0 ml aliquots were dispensed to assay tubes. Simularly, hGH was serially diluted, but over a range from 3 $\mu$M to 0.004 $\mu$M. Aliquots (10 $\mu$l) of hGH dilution (giving 1:2 molar ratio hGH to S237C-AF) and buffer only were added to the S237C-AF containing assay tubes (in triplicate), mixed and incubated to equilibrium for 5 hours at 25° C. in dark. After equilibration, fluorescence was measured as previously described (FIG. 8) except excitation bandwidth was 10 nM. IC$_{50}$ values are calculated as the concentration of hGH giving half-maximal $\Delta$F/Fo values.

In Table 2, the IC$_{50}$ values for S237C-AF dimerization induced by various homolog substitution and deletion mutants of hGH are shown. Identities of hGH mutants are given as $\Delta$, deletions and hPL, substitutions with human placental lactogen and hPRL, substitutions with human prolactin. Regions deleted or substituted are designated within parenthesis. IC$_{50}$ values are determined as described for FIG. 2. Standard deviations are generally less than +/−50% of the reported value.

TABLE 2

Receptor dimerization determinants homolog-scan

| Mutant | Dimerization IC$_{50}$ | IC$_{50}$mutant IC$_{50}$ wt |
|---|---|---|
| wt hGH | 0.54 | — |
| $\Delta$ (1–8) hGH | | >100 |
| hPRL (12–19) | 10 | 19 |
| hPRL (22–33) | .66 | 1.2 |
| $\Delta$ (32–46) | .42 | 0.8 |
| hPL (46–52) | .94 | 1.7 |
| hPRL (54–74) | 2.5 | 4.7 |
| hPRL (88–95) | .72 | 1.3 |
| hPRL (97–104) | 1.6 | 2.9 |
| hPL (109–112) | 3.0 | 5.5 |
| hPRL (111–129) | | >100 |
| hPRL (126–136) | 1.2 | 2.2 |
| hPRL (137–145) | .69 | 1.3 |
| hPRL (146–152) | .51 | 0.9 |

Initially, a series of homolog-scan hGH mutants, with hPL and hPRL segment substitutions, were tested in the S237C-AF based assay (table 2). Three of these, hPRL(12–19), hPRL(54–74) and hPRL(111–129) caused signifigant reductions (18, 6 and >100 fold, respectively) in hormone induced hGHbp dimerization. However, hPRL12–19 and hPRL54–74 disrupt residues crucial for primary site binding and have been shown to substantially reduce hGHbp affinity for this site. Losses in primary site binding for these mutants appear to largely account for the observed reductions in hGHbp dimerization. Indeed, the 500 pM IC$_{50}$ observed for S237C-AF homoquenching by wild-type hGH is nearly identical to that reported for primary site hGHbp affinity (Kd=400 pM). Furthermore, mutations of primary site determinants (eg R64A and K172A/F176A) which reduce binding affinity have also been shown to reduce dimerization, and an hGH mutant (E174A) shown to enhance hGHbp affinity for the primary site also enhances dimerization as measured in our assay. The other homolog mutant, hPRL (111–129), although uneffected for primary site binding, shows evidence of heterogeneity when analyzed by size exclusion chromatography, with 90% forming only hGH hGHbp complex, but the remaining 10% forming hGH. (hGHbp)$_2$. The existence of a sub-fraction of this mutant with relatively intact secondary site binding suggest this mutant's effects may be attributable to protein misfolding or post translational modification.

In addition to the homolog-scan mutants, two hGH deletion analogs, one removing 8 residues from the N-terminus [Δ(1–8)] and the other, a natural variant (20K hGH, U.S. Pat. No. 4,446,235) deleting residues 32–46, were tested (table 2). The Δ(1–8) mutant showed a dramatic reduction (>100 fold) in ability to induce hGHbp dimerization. Since this mutant has only a small effect on primary site binding ($Kd_{mut}/Kd_{wt}=4$), the loss in hGHbp dimerization appeared to be due to disruptions in secondary site hGHbp binding.

EXAMPLE 5

Alanine Scanning of hGH Variants

To elucidate specific side chains involved in secondary site hGHbp binding we probed the domains identified in the Δ(1–8), hPRL(11–19) and hPRL(111–129) mutants by alanine scanning. Since the two domains identified by the homolog substitutions are helical, based on the X-ray crystal structure of porcine growth hormone and are highly amphipathic, we focused the mutants screened on those located at the hydrophilic surface of these helices, where the residues are likely to be solvent exposed. In addition to these domains we also screened 3 mutants near the C-terminus (E186A, S188A and F191A) since we lacked an appropriate homolog substitution analog in this region.

From a set of 26 alanine mutants (table 3) we found two mutants, F1A and I4A which cause large disruptions in hGHbp dimerization (33 and 56 fold, respectively and four others causing ≧2-fold reductions (L6A, R8A, D116A, E119A). The alanine scan shows that residues adjacent to F1A and I4A in the N-terminal domain, as well as residues in the C-terminal domains of helices A and C, do not contribute significantly to secondary site hGHbp binding. Additional data from an hGH analog [Δ(1,2], deleting F1 and P2 from the N-terminal domain show Δ(1,2) does not disrupt dimerization any further than does F1A alone, indicating that the phenyalanine side chain is important, not the N-terminal amine or carbonyl group. The alanine scan analysis reveals that the hGH determinants most responsible for secondary site hGHbp binding and receptor dimerization are the hydrophobic side chains at F1 and I4. These determinants are strikingly different from those crucial for primary site binding, which consist of many residues (Matthews, B. W. *J. Mol. Biol.* 33:491–497 (1968)) of predominantly hydrophilic character (Boutin J. M. et. al., *Cell* 69:(1988)).

In Table 3, the IC$_{50}$ values for S237C-AF dimerization induced by alanine substituted hGH mutants are shown. Mutants are named by the wild type residue and position in the amino acid sequence, followed by the mutant residue (alanine in this case). Amino acids are designated by single letter code as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp and Y, Tyr. A mutant not expressed is designated NE. IC$_{50}$ numbers are calculated as described in FIG. 2. Standard deviations are generally less than +/−50% of the reported value or as stated.

TABLE 3

Receptor dimerization functional determinants
Alanine scanning mutagenesis

| Hormone | Dimerization IC$_{50}$ | IC$_{50}$mutant / IC$_{50}$ wt |
|---|---|---|
| wt hGH | 0.54 | — |
| F1A | 7.5 | 14 |
| P2A | .58 | 1.1 |
| T3A | .72 | 1.3 |
| I4A | 30 | 55 |
| P5A | .92 | 1.7 |
| L6A | 1.4 | 2.5 |
| S7A | .37 | 0.7 |
| R8A | 1.8 | 3.4 |
| F10A | .77 | 1.4 |
| D11A | NE | |
| N12A | .59 | 1.1 |
| L15A | .36 | 0.7 |
| R16A | .63 | 1.2 |
| H18A | .55 | 1.0 |
| R19A | .92 | 1.7 |
| H21A | .51 | 1.0 |
| D107A | .38 | 0.7 |
| N109A | .35 | 0.7 |
| Y111A | 1.0 | 1.9 |
| D112A | .53 | 1.0 |
| K115A | .84 | 1.6 |
| D116A | 3.1 | 5.7 |
| E118A | .96 | 1.8 |
| E119A | 1.1 | 2.0 |
| Q122A | .4 | 0.7 |
| T123A | .65 | 1.2 |
| R127A | .80 | 1.5 |
| E129A | .70 | 1.3 |
| D130A | .42 | 0.8 |
| E186A | .58 | 1.1 |
| S188A | .49 | .9 |
| F191A | | |

EXAMPLE 6

Homoquenching of Fluoresence

Sequential hGH additions are made to a fixed concentration of S237C-AF (100 nM), and fluorescence homoquenching monitored in real time (Example 4), show rapid equilibration times (<3 minutes) for hGH induced dimerization and slow equilibration times (>30 minutes) for subsequent reversal of dimerization by excess hGH (i.e. hGH/hGHbp>0:5) This suggests that reversal of dimerization is off-rate limited according to the mechanism

Figure 10:
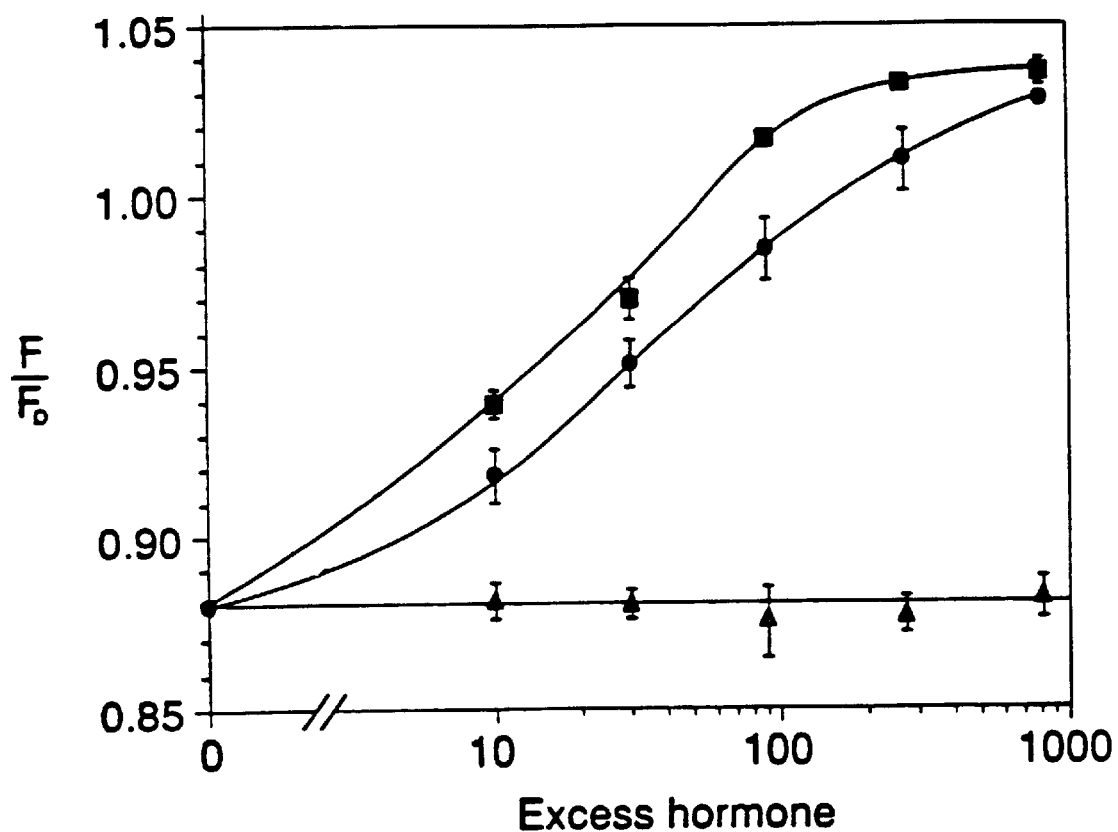
FIG. 10 Reversal of hGH induced S237C-AF dimerization by excess hGH or hGH mutants. S237C-AF and hGH were diluted in binding buffer to a concentration of 10 nM and 5 nM, respectively, and 1.0 ml aliquots dispensed to assay tubes. Serial dilutions of either hGH, mutant, or buffer only were then added and the mixture incubated to equilibrium for 5 hours at 25° C. in the dark, and fluorescence measured as described for FIG. 8. Data points are means of triplicate measurements and represent: ●, hGH; ▲, K172A/F176A; ■, hPL recruit.

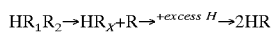

where stoichiometric binding competes with dimerization under conditions of excess hGH (H=hGH, R=free hGHbp, R$_1$=primary site hGHbp, R$_2$=secondary site hGHbp). We know primary site stoichiometric binding occurs and therefore should compete with hGH(hGHbp)$_2$ complex formation. To determine if stoichiometric secondary site binding can occur we tested an analog, engineered to remove the primary site, for ability to compete for dimerization. K172A/F176A, a double mutant with mutations in the middle of the primary site which reduce hGHbp affinity 500 fold, retains the secondary site. FIG. 10 shows that hGHbp dimerzation can not be reversed by excess K172A/F176A even when present at a 160 fold excess (800 nM). By contrast a known hPL variant, containing an engineered primary site but lacking secondary site determinants efficently blocks dimerization with an $IC_{50}$ of 20 nM (4 fold excess). This data demonstrates that stoichiometric secondary site binding does not occur and that dimerization must proceed by the sequential binding mechanism:

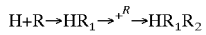

Since secondary site hGHbp binding requires stoichiometric primary site complex formation this binding event must be dependent upon determinants present in hGH. (hGHbp) and not hGH alone. As such these determinants must be introduced from primary site hGHbp and/or a conformational change elicited by the first hGHbp binding event.

EXAMPLE 7 hGH.hGHbp Amino Acid Interaction Based on X-ray Crystallography

The formation of $hGH(hGHbp)_2$ crystals permits the determination of the three-dimensional structure of the hGH $(hGHbp)_2$ complex using x-ray chrstallographic techniques following the methods described in Blundell and Johnson, Academic Press, London, 1976. Crystals of the complex were grown using a combination of vapor diffusion in sitting drops along with repeat seeding. The crystal stock solution was prepared by adding hGHbp to the met.hGH in a slight 2:1 molar excess and allowed to incubate at 4° C. for 24 hrs. The complex was then concentrated and loaded onto a size exclusion column (G75–120 Sephadex (Sigma)) that was equilibrated with 120 mM NaCl, 20 mM sodium acetate pH 5.5, 1 mM PMSF. The fractions containing the complex were then pooled, concentrated and desalted onto 50 mM sodium acetate pH 5.5, 1 mM PMSF. The concentration of the complex in the resulting stock solution was 4 mg/ml ($E_{280}$ (0.1%)=1.67 $cm^{-1}$). The stock solution of complex was diluted to 1.7 mg/ml using 0.1M Bis.tris pH 6.5, to which saturated ammonium sulfate (ultrapure (Schwarz-Mann)) was added to make a 10% saturated solution. MPD(Aldrich) was added to a final concentration of 1%. Fifty microliters of the mixture were then pipetted into a Pyrex glass spot plate and allowed to equilibrate against 40% saturated ammonium sulfate for 2 days at room temperature in a 150 mm×25 mm plastic culture dish before seed crystals were introduced. Within two weeks, crystals were obtained with dimensions of 1 mm×0.5 mm×0.1 mm, that diffract to 2.7 Å on a rotating anode generator operated at 45 kV, 110 mA.

The three dimensional polypeptide structure of the hGH $(hGHbp)_2$ crystal structure is illustrated in FIG. 11. The central top region, in thicker fines, represents the hGH molecule; the alpha helices are clearly visible. This hGH molecule is bound to two hGHbp molecules: one at the left hand side, and one at the right. Each of these hGHbp molecules has two domains linked by a single strand; the top domains are at the same height as the hGH molecule, the other domains are oriented vertically and stick out towards the bottom of the figure; These last two domains of the hGHbp contact each other at the very bottom of FIG. 11. This contact at the bottom constitutes the only contact region between the two hGHbp molecules and the points of contact are discussed below. Based upon this structure an analysis of the interacting amino acids of the three polypeptides was made. They fall into three categories: 1) interactions between hGH and hGHbp1 (the first hGHbp to bind) listed in Table 4; 2) interactions between hGH and hGHbp2 (second hGHbp to bind) listed in Table 5; and 3) interactions between the two hGHbp in the complex listed in Table 6. Tables 4 and 5 disclose the unique individual hGH amino acids binding to the indicated unique hGHbp amino acids. The particular moiety bound and the nature of the chemical interaction are also listed. The nomenclature follows standard amino acid single letter nomenclature and the number of the amino acid when numbered from the amino terminus of the natural hGH or hGHpb. The remaining terms in Tables 4, 5 and 6 are defined as follows: MC=main chain, SC=side chain, SS=disulfide, HB=hydrogen bond, SB=salt bridge, VW=van der Waals. These tables are not exclusive of all site 1 and 2—affecting residues.

TABLE 4

SITE 1 Interactions

| hGH | moiety | hGHbp1 | moiety | Interaction |
|---|---|---|---|---|
| H18 | SC | R217 | SC. | VW |
|  | SC | N218 | SC | VW |
| H21 | SC | N218 | MC | VW |
|  | SC | N218 | SC | VW |
| Q22 | MC | N218 | SC | VW |
| F25 | SC | S119 | MC | VW |
|  | SC | G120 | MC | VW |
| K41 | SC | E127 | SC | SB |
| Y42 | SC | K121 | MC | VW |
|  | SC | K121 | SC | VW |
|  | SC | C122 | MC | VW |
|  | SC | C122 | SC | VW |
| L45 | SC | P106 | SC | VW |
|  | SC | C122 | MC | VW |
| Q46 | SC | E120 | SC | HB |
|  | SC | C108–C122 | SS | VW |
| P61 | SC | S102 | MC | VW |
|  | SC | S102 | SC | VW |
| S62 | SC | R43 | MC | HB |
|  | SC | E244 | SC | VW |
|  | SC | W169 | MC | VW |
| N63 | MC | W169 | SC | VW |
|  | SC | W169 | SC | VW |
|  | SC | E244 | SC | VW |
| E66 | SC | W169 | SC | VW |
| R167 | SC | E127 | SC | SB |
| K168 | SC | W104 | MC | HB, VW |
|  | SC | W104 | SC | VW |
| D171 | SC | R43 | SC | SB |
|  | SC | W104 | SC | VW |
| K172 | SC | W104 | MC | VW |
|  | SC | W104 | SC | VW |
| T175 | SC | R43 | SC | HB |
|  | SC | W104 | SC | VW |
|  | SC | W169 | SC | VW |
| R178 | SC | I165 | MC | HB |
|  | SC | G168 | MC | VW |
| C182–C189 | SS | K167 | MC | VW |

TABLE 5

SITE 2 Interactions

| hGH | moiety | hGHbp2 | moiety | Interaction |
|---|---|---|---|---|
| T3 | SC | P106 | SC | VW |
| I4 | SC | F123 | MC | VW |
| L6 | SC | S124 | SC | VW |
| L9 | SC | W104 | SC | VW |
| N12 | SC | R143 | SC | HB |
|  | SC | W169 | SC | VW |
|  | MC | W169 | SC | VW |
| L15 | SC | W169 | SC | VW |
| R16 | SC | W169 | SC | VW |
|  | SC | E44 | SC | SB |

TABLE 5-continued

SITE 2 Interactions

| hGH | moiety | hGHbp2 | moiety | Interaction |
|---|---|---|---|---|
| R19 | SC | N166 | SC | HB |
| | SC | K167 | MC | VW |
| | SC | K167 | SC | VW |
| Q22 | SC | Q166 | SC | VW |
| Y103 | SC | Y164 | MC | VW |
| | SC | I165 | SC | VW |
| | SC | N166 | MC | VW |
| N109 | SC | K167 | SC | HB |
| D116 | SC | W104 | SC | VW |
| E119 | SC | W104 | SC | VW |
| | SC | S102 | SC | HB |
| G120 | MC | W104 | SC | VW |
| T123 | SC | W104 | SC | VW |

TABLE 6

Binding Protein Interactions

| hGHbp1 | moiety | hGHbp2 | moiety | Interaction |
|---|---|---|---|---|
| S145 | SC | D152 | SC | VW |
| | SC | Y200 | SC | VW |
| L146 | SC | H150 | SC | VW |
| | MC | S201 | SC | HB |
| T147 | SC | H150 | SC | VW |
| | SC | D152 | SC | HB |
| H150 | SC | L142 | SC | VW |
| | SC | N143 | SC | HB |
| | SC | D152 | SC | VW |
| | SC | Y200 | SC | VW |
| D152 | SC | Y200 | SC | HB |
| Y200 | SC | L192 | SC | VW |
| | SC | V197 | SC | VW |
| | SC | P198 | SC | VW |
| S201 | MC | P198 | SC | VW |
| | MC | Y200 | SC | HB? |
| | MC | Y200 | SC | VW |

EXAMPLE 8

Use of Monoclonal Antibody to Stimulate hGH Receptor

The assay of the present invention may be used to screen monoclonal antibodies that are directed against growth hormone receptors. The resulting monoclonal antibodies can then be evaluated in vivo for relative ability to promote growth. The monoclonal antibody MAb 263 (Agen Biochemical Ltd, Queensland, Australia) was made using as an immunogen the glycosylated rat and rabbit receptor. When MAb263 was administered daily by s.c. injection to hypophysectomized rats, at a dosage equivalent on a molar basis to an hGH dose of 155 µg/Kg in rat, there was a significant body weight gain as shown in FIG. 12.

Two groups of eight rats each were given excipient buffer (10 mM Tris, pH 8, 0.1% bovine serum albumin) either with or without MAb 263 (1.05 mg/kg). The rats were given food and water on demand. Daily weight is shown in FIG. 12. At the end of day six the rats were weighed with the results in Table 7 below.

TABLE 7

Monoclonal Antibody Induced Weight Gain

| Group | Body Weight Gain/Rat | Percent Weight Gain |
|---|---|---|
| MAb283 | 6.075 g +/− 1.97 g | 6.47 +/− 1.97% |
| Control | 0.9875 g +/− 2.16 g | 1.01 +/− 2.30% |

Therefore, monoclonal antibody directed against the growth hormone receptor can be administered to produce weight gain.

EXAMPLE 9

Cellular Assay for Agonist or Antagonist Activity

A novel cell-based bioactivity assay system is provided herein. It is based on a hybrid receptor (U.S. Pat. No. 4,859,609) transformed cell line that comprises an extracellular, GH-binding domain of the GH receptor fused at its C-terminus to a hormone or cytokine receptor, e.g., that of EPO, alpha interferon, beta interferon, GM-CSF, C-CSF, prolactin, placental lactogen or interleukins 2, 3, 4, 6 or 7, the cell line ordinarily being responsive to the hormone or cytokine and ordinarily containing the receptor for the hormone or cytokine. Usually, only the transmembrane and endoplasmic portions of the hormone or cytokine receptor are used, fused at their N-terminus to the GH receptor fragment. The responsive feature of the cell is any measurable characteristic, e.g., changes in membrane characteristics, proliferation, mitotic features, release of analytes (e.g., degranulation) and the like.

The hGH receptor belongs to a large family of receptors of hematopoietic origin (7), that includes the interleukin-3 (IL-3) and granulocyte colony stimulating factor (G-CSF) receptors. Nagata and coworkers (8) showed that an IL-3 dependent myeloid leukemia cell-line (FDC-P1) transfected with the full-length murine G-CSF receptor proliferates by addition of G-CSF without IL-3. A hybrid receptor (U.S. Pat. Nos. 4,859,809 and 5,030,576) was constructed by Drs. Etsuko Ishizaka-Ikeda and Shigekazu Nagata of the Osaka Bioscience Institute containing the hGHbp linked to a form of the mG-CSF receptor missing the G-CSF binding domain but containing the three extracellular fibronectin repeats, the transmembrane and intracellular domains. The fibronectin domains are not involved in binding of G-CSF but are required for good expression of the mG-CSF receptor (8).

The hybrid receptor was constructed from cDNA containing exons 1 through 5 of the hGH receptor (that encodes the secretory signal and the extracellular hGH binding domains) linked to exons 7 through 15 of the mG-CSF receptor (that encodes the three fibronectin domains plus the entire transmembrane and intracellular domains). Sequences derived from the hGH receptor (Leung D., et al., Nature 330:537 (1987)) were cloned by PCR into the vector, pBOS-I62 (8), which allowed expression of the hybrid receptor in FDC-P1 cells. A single cysteine was produced at the junction of the two receptor fragments. Transfection and culturing of stable FDC-P1 cell-lines were as described (infra).

Competitive displacement of [$^{125}$I]hGH from hybrid-receptors on whole cells was used to establish the affinity and the approximate number of receptors per cell. Cells grown with IL-3 were washed before assay with phosphate buffered saline (PBS) plus 10% FBS. Cells were incubated (1.2×10$^6$/ml) with serial dilutions of hGH in the presence of 20 pM [$^{125}$I]hGH (Y103A) for 18 h at 4° C. Cells were then washed with PBS twice to remove the excess label. Y103A was used to prevent iodination of Y103 which would partially block the binding of the second hGHbp (9).

In several independent binding experiments the apparent $K_d$ value for hGH was 0.1±0.03 nM and there were 1000±300 receptors per cell. This affinity is about 34-fold stronger than hGH binding to the soluble hGHbp and may reflect an avidity effect for binding of hGH to receptors on cells. Non-transfected cells lacked specific binding sines for hGH (9). FIG. 13 shows the effect of increasing hGH concentrations on the ability of hGH to induce cell proliferation. At low concentrations, hGH acts as a potent agonist in this assay with an $EC_{50}$ of ~20 pM, a value somewhat lower than the apparent $K_d$ on whole cells (~100 pM). This could reflect that maximal cell-proliferation may occur at less than 100% receptor occupancy.

Mutational analysis (3, 4) and structural studies (5) show that each hGH molecule is bivalent in that it contains two separate sites for binding the hGHbp. In contrast, the hGHbp is effectively univalent because each uses virtually the same determinants to bind either Site 1 or Site 2 on hGH. Excess hGH will dissociate the hGH.(hGHbp)$_2$ complex to form a hGH.hGHbp complex in which hGH is bound exclusively via Site 1 to the hGHbp. Thus, we predicted that excess hGH should antagonize signaling (FIG. 1). Indeed, at very high hGH concentrations the proliferation activity is lost ($IC_{50}$@2 μM). IL-3 induced cell proliferation is not altered in the presence of high concentrations of hGH (8 μM) indicating hGH is not toxic to cell proliferation. Neither the agonist nor antagonist inflection points depend on the cell density (FIG. 13) indicating the effect does not involve cross-linking receptors between cells or other cell-cell interactions. Furthermore, FDC-P1 cells containing the full-length mG-CSF receptor do not respond to hGH, and neither do cells containing the hybrid receptor respond to G-CSF.

EXAMPLE 10

To further investigate the requirement for dimerization of the hGHbp for signaling in the hybrid receptor cell proliferation assay we utilized bivalent monoclonal antibodies (MAbs) and univalent fragments derived from them (FAbs) that were directed against the hGHbp. Addition of increasing concentrations of three of four different anti-receptor MAbs at low concentrations were as potent as hGH in inducing cell proliferation (Table 8).

TABLE 8

Summary of dose response data for a variety of anti-hGH receptor MAbs, FAbs (16) and hGH mutants (17) to stimulate proliferation of FDC-P1 cells containing the hGH-mG-CSF hybrid receptor. None indicates no effect was observed and ND indicates not determined.

| Protein | $K_d$ (nM)* | $EC_{50}$† | Max. response relative to hGH | Self-antagonism‡ |
|---|---|---|---|---|
| MAb263 | 0.6 | 0.3 nM | (110) | >10 μM |
| MAb13E1 | 3.2 | 0.8 nM | (100) | >>10 μM |
| MAb3D9 | 2.2 | 0.8 nM | (80) | 0.2 μM |
| MAb5 | 0.7 | ~1 nM | (10) | 20 nM |
| FAb263 | ND | >1.5 μM | | ND |
| FAb13E1 | ND | >3 μM | | ND |
| FAb3D9 | ND | >0.1 μM | | ND |
| FAb5 | ND | >1 μM | | ND |
| hGH | 0.3 | 20 pM | | 2 μM |

TABLE 8-continued

Summary of dose response data for a variety of anti-hGH receptor MAbs, FAbs (16) and hGH mutants (17) to stimulate proliferation of FDC-P1 cells containing the hGH-mG-CSF hybrid receptor. None indicates no effect was observed and ND indicates not determined.

| Protein | $K_d$ (nM)* | $EC_{50}$† | Max. response relative to hGH | Self-antagonism‡ |
|---|---|---|---|---|
| K172A/F176A | 200 | 25 nM | | None |
| G120R | 0.3 | None | | — |
| H21A/R64K/E174A | 0.01 | 20 pM | | 60 nM |
| H21A/R64K/E174A/G120R | 0.01 | None | | — |

*$K_d$ values for MAbs binding to the hGHbp were taken from ref. 13. $K_d$ value for hGH and variants were measured using a [$^{125}$I]hGH competitive displacement assay where hormone bound to hGHbp was precipitated with MAb5 (4, 12). This gives the affinity for the monomeric hGH-HGHbp complex.
‡Values for $EC_{50}$ were taken from titration curves shown for example in FIG. 13 (except for FAbs which are not shown) and represent the half-maximal concentration for stimulation of cell proliferation. Data are the mean of triplicate tubes and the S.D. are within 15% of mean.

Values shown with ">" indicate that we could not go to high enough concentrations of protein to complete the titration curve. For these cases we only report limit estimates of the $EC_{50}$. ‡Self-antagonism refers to the half-maximal concentration leading to inhibition of cell-proliferation at high concentration.

MAb5 and 263 were from Agen, Inc. (New Jersey) and have been described by Waters and coworkers (Barnard, R., et al., *Endocrinology* 115:1805–1813 (1984); Barnard, R., et al., *Biochem. J.* 231:459–468 (1985). MAbs 13E1 and 3D9 were from the Genentech hybridoma group and their properties have been described elsewhere (3). Briefly, MAbs were purified from mouse ascites fluid by binding to Protein-A Sepharose and elution with 0.1 M acetate (pH 3.0). FAb fragments were prepared by treating MAbs with dithiothreitol-activated papain (50:1 wt MAb/wt papain) in PBS plus 10 mM cysteine for 1 h. Digestions were stopped by adding 0.1 M iodoacetamide. The Fc and residual MAb was removed by adsorption onto Protein-A Sepharose twice, followed by gel filtration on Superose 12 (Pharmacia).

The EC50 value for each MAb (0.3 to 1 nM) was usually somewhat less than the $K_d$ as determined by ELISA (Table 8). As with hGH, this may reflect avidity effects on whole cells, and/or that maximal signaling is achieved at less than 100% receptor occupancy. At much higher concentrations (20 nM lo >10 μM) two of these MAbs lost activity presumably because excess MAb blocks receptor cross-linking due to monovalent attachment to hGHbp. Corresponding monovalent FAb fragments were virtually inactive (Table 8) further indicating that bivalency is required for signaling activity.

The differences in dose response curves for these MAbs can be explained by the different ways they bind to the hGHbp. MAb5 prevents binding of a second hGHbp to the hGH.hGHbp complex (3), possibly by binding to the region where both receptors contact each other (FIG. 11). The fact that MAb5 is the least efficient may indicate the receptors need to closely approach each other for maximal signaling. MAb13E1 blocks hGH binding (11) and mimics the effect of hGH. This MAb showed a broad plateau and no antagonistic phase probably because we could not go to high enough MAb concentrations to observe one. We suggest this neutralizing MAb binds like hGH to form very stable receptor dimers. In contrast, MAbs 263 and 3D9 bind away from the hormone-receptor interfaces and show similar agonistic and antagonistic phases. These two phases are not as widely separated as for hGH perhaps because the dimers do not have the optimal receptor-receptor contacts. The fact that MAbs 263 and 3D9 are agonists suggest that the structural requirements to form active dimers are rather loose.

FAb fragments derived from MAb13E1 or MAb5 antagonize hGH-induced cell proliferation whereas those derived from MAbs 263 and 3D9 do not (Table 9). These studies are consistent with the fact that the epitopes for MAb 13E1 and MAb 5 block hormone-receptor or receptor-receptor interfaces.

TABLE 9

Summary of antagonist effects of FAbs and hGH analogs that block hGH-induced cell proliferation of FDC-P1 cells containing the hybrid hGH-mG-CSF receptor. Cells were incubated with 1 nM hGH plus increasing concentrations of FAb or hGH analog The half-maximal inhibitory concentration is that required to block 50% of the cell-proliferation activity of hGH. None indicates no inhibition was observed for up to 10 μM FAb or hGH analog.

| Protein | $IC_{50}$ |
|---|---|
| FAb263 | None |
| FAb13E1 | 0.8 μM |
| FAb5 | 0.2 μM |
| FAb3D9 | None |
| hGH | 2 μM |
| K172A/F176A | None |
| G120R | 20 nM |
| H21A/R64K/E174A | 60 nM |
| H21A/R64K/E174A/G120R | 2 nM |

EXAMPLE 11

To further determine the structural requirements on hGH for dimerization (FIG. 11) we examined mutants of hGH that were designed to reduce binding of receptors to Site 1 or Site 2. The double mutant (K172A/F176A), which preserves Site 2 determinants but alters important side-chains in Site 1 (12), promotes cell proliferation but the $EC_{50}$ is shifted to a concentration about $10^3$-fold higher than wild-type hGH (Table 8). This is consistent with the 560-fold reduction in the $K_d$ for Site 1 binding as measured in vitro (12). We could not go to high enough concentrations to observe an inactive phase in the titration with K172A/F176A. The single hGH mutant (G120R) retains a functional Site 1 but sterically blocks Site 2. This mutant is virtually inactive at any concentration. Thus, binding to either Site 1 or Site 2 is necessary but not sufficient for promoting cell proliferation.

The sequential signaling mechanism predicts that mutants blocked in Site 2 binding but not Site 1 binding) should antagonize hGH-induced cell proliferation. To test this we cultured cells with enough hGH (1 nM) to support 90% of maximal cell proliferation plus increasing concentrations of wild-type hGH or the mutants in Site 1 (K172A/F176A) or Site 2 (G120R). As we expected the Site 2 mutant antagonizes hGH whereas the Site 1 mutant is totally ineffective. In fact, the Site 2 mutant is nearly 100-fold more potent as an antagonist than wild-type hGH ($IC_{50}$ is 20 nM for G120R versus 2 μM for hGH; Table 9). This was not unexpected to us because once G120R is bound it can not dimerize and agonize the receptor. Thus, competition between G120R and hGH is more confined to free hormone molecules binding through Site 1. In contrast, for hGH to be antagonistic free hormone needs to react with unoccupied receptors before bound hGH intermediate does. This requires high concentrations of hGH.

Although G120R is a much better antagonist than hGH, the concentration of mutant required for 50% antagonism was about 20-times higher than that of hGH in the assay (Table 9). This may reflect the fact that hGH is bound more tightly in the dimeric hGH.(receptor)$_2$ complex than G120R is in the monomeric G120R.receptor complex. Alternatively, maximal signaling may not require 100% receptor occupancy. In either case improving the affinity for Site 1 in the G120R mutant will make it a more potent antagonist.

hGH variants have been produced by mutagenesis (4, 13) that bind more tightly to the hGHbp via Site 1. A combination of these variants (H21A/R64K/E174A) binds 30-times more tightly to the hGHbp (Table 9). This variant had an $EC_{50}$ comparable to hGH but an $IC_{50}$ for self-antagonism that is about 30 times lower than hGH. This is consistent with the notion that self-antagonism results from competition between Site 2 on bound hormone-receptor intermediate and free Site 1 on the soluble hormone. The fact that improving Site 1 binding did not improve this hormone as an agonist could reflect that receptor dimerization is rate limiting and that it therefore is desirable to introduce agonist mutations into both Sites 1 and 2. We further mutated this variant to contain G120R. The tetra-mutant variant was 10-fold more potent than G120R as an hGH antagonist (FIG. 14, Table 9). This is further evidence for the importance of Site 1 binding affinity for antagonism.

Our studies indicate that the antagonism or self-antagonism caused by hGH, MAbs and their derivatives is the result of blocking receptor dimerization and not receptor-down regulation. Firstly, cells propagated with IL-3 instead of hGH do not show a greater hGH response or hGH receptor number. Receptor down-regulation is usually tightly coupled to receptor activation. In this case one may expect the antagonistic portion of the dose response curve for hGH to start at physiologically relevant concentrations of hGH (not 1 μM). Moreover, the ratio of $EC_{50}$ to $IC_{50}$ for each of the MAbs and hGH varies widely showing that receptor activation can be readily uncoupled from inhibition by simply altering binding properties. Finally, the G120R mutant is inactive yet it is a more potent antagonist than hGH, and pretreatment of cells with G120R does not enhance its antagonistic effect. Thus, the antagonistic effect of G120R is not consistent with simple receptor down-regulation. It is possible that other ligands that exhibit self-antagonism at high concentrations may involve blocking of receptor dimerization, and this serves as an additional basis for identifying ligands that are useful in the practice of this invention.

Citations

1. Melmed, S., *New Engl. J. Med.* 322:966–977 (1990); Frohman, L. A., *J. Clin. Endo. Metab.* 72:1175–1181 (1991).
2. Wells, J. A., et al., *Recent Prog. Hormone Res.* 52, in press (1992).
3. Cunningham, B. C., et al., *Science* 254:821–825 (1992).
4. Cunningham B. C., et al., *Science* 244:1081–1085 (1989).
5. de Vos, A. M., et al., *Science* 255:306–312 (1992).
6. Yarden Y., et al., *Ann. Rev. Biochem.* 57:443 (1988); Ullrich A., et al., *Cell* 61:203 (1990).
7. Bazan, J. F., *Proc. Natl. Acad. Sci. U.S.A.* 87:6934 (1990); Cosman D. et al., *Trends Biochem. Sci.* 15:265 (1990); Patthy, L. *Cell* 61:13 (1990).
8. Fukunaga, R., et al., *EMBO J.* 10:2855–2865 (1991).
9. Bass, S. H., et al., *Proc. Natl. Acad. Sci. U.S.A.* 88:4498–4502 (1991).
10. Cunningham B. C., et al., *Proc. Natl. Acad. Sci. U.S.A.* 88:3407–3411 (1991).

11. Cunningham, B. C., et al., *Science* 247:1461–1465 (1990).
12. Elberg, et al., *JBC*. 265:14770 (1990)
13. N. Itoh, et al., *Science* 247:324 (1990)

What is claimed is:

1. A variant of a native mature mammalian growth hormone, said variant having a non-naturally occurring growth hormone amino acid sequence or a covalent modification, comprising a mutation selected from the group consisting of:
   (a) an amino acid substitution at a residue corresponding to residue 1 of human growth hormone, numbered from the N-terminus;
   (b) an amino acid substitution at a residue corresponding to residue 4 of human growth hormone, numbered from the N-terminus, wherein the substituted amino acid is selected from the group consisting of R, N, D, C, Q, E, G, H, K, M, F, P, S, T, W, Y, and V;
   (c) an amino acid substitution at a residue corresponding to residue of 6 of human growth hormone, numbered from the N-terminus, wherein the substituted amino acid is selected from the group consisting of R, N, D, C, Q, E, G, H, I, K, M, F, P, S, T, W, Y, and V;
   (d) an amino acid substitution at a residue corresponding to residue 8 of human growth hormone, numbered from the N-terminus, wherein the substituted amino acid is selected from the group consisting of N, D, C, Q, E, G, H, I, L, K, F, P, S, T, W, Y, M, and V;
   (e) insertion of an amino acid adjacent to a residue corresponding to a residue of human growth hormone selected from the group consisting of 1, 4, 6, and 8, numbered from the N-terminus; and
   (f) covalent modification of a residue corresponding to a residue of human growth hormone selected from the group consisting of 1, 4, 6, and 8, numbered from the N-terminus.

2. The variant of claim 1 wherein said mutation alters the ability of said variant to bind two receptor polypeptides so that said variant binds to a target for said native mature mammalian growth hormone with an affinity different from the affinity of said native mature mammalian growth hormone for said target.

3. The variant of claim 1 wherein said native mature mammalian growth hormone is human growth hormone.

4. The variant of claim 3 wherein said mutation is selected from the group consisting of:
   (a) an amino acid substitution at I4, numbered from the N-terminus, wherein the substituted amino acid is selected from the group consisting of V and M; and
   (b) an amino acid substitution at R8, numbered from the N-terminus, wherein the substituted amino acid is selected from the group consisting of V and I.

5. The variant of claim 3 wherein said mutation is selected from the group consisting of:
   (a) an amino acid substitution at F1, numbered from the N-terminus, wherein the substituted amino acid is selected from the group consisting of D, E, N, Q, P, G, A, V, L, I, M, S, and T;
   (b) an amino acid substitution at I4, numbered from the N-terminus, wherein the substituted amino acid is selected from the group consisting of K, R, H, D, E, N, Q, F, Y, W, S, and T;
   (c) an amino acid substitution at L6, numbered from the N-terminus, wherein the substituted amino acid is selected from the group consisting of K, R, H, D, E, N, Q, F, Y, W, S, and T; and
   (d) an amino acid substitution at R8, numbered from the N-terminus, wherein the substituted amino acid is selected from the group consisting of D, E, F, Y, W, P, G, V, L, I, and M.

6. A variant of a native mature mammalian growth hormone, said variant having a non-naturally occurring amino acid sequence or a covalent modification, comprising:
   (a) a first mutation in a first region corresponding to residue 1 to residue 15 of human growth hormone, numbered from the N-terminus; and
   (b) a second mutation in a second region corresponding to residue 106 to residue 128 of human growth hormone, numbered from the N-terminus.

7. The variant of claim 6 wherein said first and second mutations alter the ability of said variant to bind two receptor polypeptides so that said variant binds to a target for said native mature mammalian growth hormone with an affinity different from the affinity of said native mature mammalian growth hormone for said target.

8. The variant of claim 6 wherein said native mature mammalian growth hormone is human growth hormone.

9. The variant of claim 8 wherein said second region extends from residue 116 to residue 123 of human growth hormone, numbered from the N-terminus.

10. The variant of claim 9 wherein at least one of said mutations is an amino acid substitution or deletion at a residue corresponding to a residue of human growth hormone selected from the group consisting of F1, I4, L6, R8, D116, D119, G120, and T123, numbered from the N-terminus.

11. The variant of claim 10 wherein said variant comprises a set of amino acid substitutions selected from the group consisting of:
   F1T, I4F, L6R, G120R, T123D;
   F1A, I4A, G120F;
   F1A, I4A, G120I, T123A;
   I4A, L6A, G120A; and
   I4A, L6A, G120A, T123A.

12. A variant of a native mature mammalian growth hormone, said variant having a non-naturally occurring amino acid sequence or a covalent modification, comprising:
   (a) a first mutation in a first region selected from the group consisting of (i) amino acid residue L15, R16, R19 and Q22, (ii) the C-terminal ⅔ of the loop linking helices 1 and 2, and (iii) the C-terminal ½ of helix 4; and
   (b) a second mutation in a second region selected from the group consisting of (i) a region corresponding to residue 1 to residue 15 of human growth hormone and (ii) a region corresponding to residue 106 to residue 128 of human growth hormone, numbered from the N-terminus.

13. The variant of claim 12 wherein said native mature mammalian growth hormone is human growth hormone.

14. The variant of claim 12 wherein said first and second mutations alter the ability of said variant to bind two receptor polypeptides so that said variant binds to a target for said native mature mammalian growth hormone with an affinity different from the affinity of said native mature mammalian growth hormone for said target.

15. The variant of claim 14 wherein said first mutation increases the ability of said variant to bind said first receptor polypeptide, and said second mutation decreases the ability of said variant to bind said second receptor polypeptide, compared to said native growth hormone.

16. The variant of claim 13 wherein said first mutation comprises an amino acid substitution at a position selected from the group consisting of R64, K172, E174, and F176 of human growth hormone, numbered from the N-terminus.

17. The variant of claim 16 wherein said variant comprises a set of amino acid substitutions selected from the group consisting of:

F1A, I4A, F10A, M14W, H18D, G120R, F, Y, W, D, E, or I, R167N, D171S or A, E174S or A, F176Y, I179T;

F1A, I4A, R64K, E174A;

I4A, G120I or R, E174A; and

R64K, G120R, E174A.

18. A variant of a native, mature mammalian monomeric polypeptide ligand having four amphipathic alpha helices, wherein said native ligand binds to a first receptor polypeptide through a first ligand site and then binds to a second receptor polypeptide through a second ligand site, thereby forming a ternary complex, said variant having a non-naturally occurring amino acid sequence or a covalent modification and comprising:

(a) a first mutation in a portion of said second ligand site corresponding to the first third of helix 1; and (b) a second mutation in a portion of a said second ligand site corresponding to the middle half of helix 3.

19. The variant of claim 18 additionally comprising an amino acid substitution in a portion of said first ligand site selected from the group consisting of (a) a region corresponding to residue 14 to residue 25 of human growth hormone, numbered from the N-terminus; (b) the C-terminal of ⅔ of the loop linking helices 1 and 2; and (c) the C-terminal ½ of helix 4.

20. A variant of a native, mature mammalian monomeric polypeptide ligand having four amphipathic alpha helices, wherein said native ligand binds to a first receptor polypeptide through a first ligand site and then binds to a second receptor polypeptide through a second ligand site, thereby forming a ternary complex, said variant having a non-naturally occurring ammo acid sequence or a covalent modification and comprising:

(a) a first mutation including an amino acid substitution in a portion of said first ligand site selected from the group consisting of (i) amino acid residue L15, R16, R19 and Q22, (ii) the C-terminal ⅔ of the loop linking helices 1 and 2, and (iii) the C-terminal ½ of helix 4; and (b) a second mutation in a portion of said second ligand site selected from the group consisting of (i) the first third helix 1 and (ii) the middle half of helix 3.

21. The variant of claim 1 wherein said variant is covalently attached to a polyethylene glycol molecule.

22. The variant of claim 6 wherein said variant is covalently attached to a polyethylene glycol molecule.

23. The variant of claim 12 wherein said variant is covalently attached to a polyethylene glycol molecule.

24. The variant of claim 18 wherein said variant is covalently attached to a polyethylene glycol molecule.

25. The variant of claim 20 wherein said variant is covalently attached to a polyethylene glycol molecule.

* * * * *